United States Patent
Ranki et al.

(10) Patent No.: US 11,690,913 B2
(45) Date of Patent: Jul. 4, 2023

(54) COMBINING ADENOVIRUS AND CHECKPOINT INHIBITORS FOR TREATING CANCER

(71) Applicant: TARGOVAX OY, Espoo (FI)

(72) Inventors: Tuuli Ranki, Riihimäki (FI); Sari Anneli Pesonen, Helsinki (FI); Magnus Jäderberg, London (GB); Elina Haavisto, Helsinki (FI); Lukasz Kuryk, Helsinki (FI); Antti Vuolanto, Veikkola (FI)

(73) Assignee: TARGOVAX OY, Espoo (FI)

( * ) Notice: Subject to any disclaimer, the term of this patent is extended or adjusted under 35 U.S.C. 154(b) by 206 days.

(21) Appl. No.: 17/141,463

(22) Filed: Jan. 5, 2021

(65) Prior Publication Data
US 2021/0121564 A1 Apr. 29, 2021

Related U.S. Application Data

(63) Continuation of application No. 16/330,274, filed as application No. PCT/FI2017/050645 on Sep. 11, 2017, now Pat. No. 10,940,203.

(30) Foreign Application Priority Data

Sep. 12, 2016 (EP) ..................................... 16188301

(51) Int. Cl.
| | | |
|---|---|---|
| *A61K 35/761* | (2015.01) | |
| *A61K 39/395* | (2006.01) | |
| *A61K 39/00* | (2006.01) | |
| *A61P 35/00* | (2006.01) | |
| *C07K 16/28* | (2006.01) | |
| *C07K 14/535* | (2006.01) | |

(52) U.S. Cl.
CPC ........ *A61K 39/3955* (2013.01); *A61K 35/761* (2013.01); *A61P 35/00* (2018.01); *C07K 14/535* (2013.01); *C07K 16/2818* (2013.01); *C07K 16/2827* (2013.01); *A61K 2039/505* (2013.01); *A61K 2039/545* (2013.01)

(58) Field of Classification Search
CPC ............ A61K 2039/505; A61K 35/761; A61K 39/00; A61K 2300/00; A61P 35/00
See application file for complete search history.

(56) References Cited

U.S. PATENT DOCUMENTS

2015/0086541 A1   3/2015   Aguilar-Cordova

FOREIGN PATENT DOCUMENTS

| WO | 2010072900 A1 | 7/2010 |
| WO | 2014036412 A2 | 3/2014 |
| WO | 2014047350 A1 | 3/2014 |
| WO | 2015077624 A1 | 5/2015 |

OTHER PUBLICATIONS

Amgen: "A Phase 1b/3, Multicenter, Open-label Trial of Talimogene Laherparepvec in Combination With Pembrolizumab (MK-3475) for Treatment of Unressected, Stage IIIB to IVM1c Melanoma (MASTERKEY-256)", Internet Citation, Jun. 22, 2015.
Andtbacka et al. "Talimogene laherparepvec improves durable response rate in patients with advanced melanoma." J Clin Oncol 33(25): 2780-2788 (2015).
Andtbacka. "The role of talimogene laherparepvec (T-VEC) in the age of checkpoint inhibitors." Clinical Advances in Hematology & Oncology: H&O 14(8): 576-579 (2016).
Choi et al. "Concurrent delivery of GM-CSF and B7-1 using an oncolytic adenovirus elicits potent antitumor effect." Gene Therapy 13(13): 1010-1020 (2006).
European Search Report from Application No. EP 16 18 8301 dated Feb. 16, 2017.
Fueyo et al. "A mutant oncolytic adenovirus targeting the Rb pathway produces anti-glioma effect in vivo." Oncogene 19(1): 2-12 (2000).
Hanahan et al. "The hallmarks of cancer." Cell 100(1): 57-70 (2000).
Heise et al. "An adenovirus E1A mutant that demonstrates potent and selective systemic anti-tumoral efficacy." Nature Medicine 6(10): 1134-1139 (2000).
International Search Report from International Application No. PCT/FI2017/050645 dated Oct. 16, 2017.
Koski et al. "Treatment of cancer patients with a serotype 5/3 chimeric oncolytic adenovirus expressing GMCSF." Molecular Therapy 18(10): 1874-1884 (2010).
Partial European Search Report from Application No. EP 16 18 8301 dated Feb. 16, 2017.
Puzanov et al. "151884-156", ASCO, Meeting Library: "Survival, safety, and response patterns in a phase 1b multicenter trial of talimogene laherparepvec (T-VEC) and ipilimumab (ipi) in previously untreated, unresected stage IIIB-IV melanoma." J Clnn Oncol 33 (suppl; abstr 9063) (2015).
Ranki et al. "Local treatment of a pleural mesothelioma tumor with ONCOS-102 induces a systemic antitumor CD8+ T-cell response, prominent infiltration of CD8+ lymphocytes and Th1 type polarization." Oncoimmunology 3(10): e958937 (2014).
Ranki et al. "Phase I study with ONCOS-102 for the treatment of solid tumors—an evaluation of clinical response and exploratory analyses of immune markers." Journal for Immunotherapy of Cancer 4(1): 17 pp. 1-18 (2016).
Romano et al. "Ipilimumab-dependent cell-mediated cytotoxicity of regulatory T cells ex vivo by nonclassical monocytes in melanoma patients." Proceedings of the National Academy of Sciences 112(19): 6140-6145 (2015).

(Continued)

*Primary Examiner* — Barry A Chestnut
(74) *Attorney, Agent, or Firm* — Nixon Peabody LLP; Elizabeih Baio; Nicole D Kling

(57) ABSTRACT

The invention relates to the combination therapy comprising oncolytic adenovirus vector and a checkpoint inhibitor or checkpoint inhibitors. More specifically, the invention relates to oncolytic adenovirus vector and checkpoint inhibitor or checkpoint inhibitors for use in a cancer therapy.

18 Claims, 9 Drawing Sheets

(56) References Cited

OTHER PUBLICATIONS

Sagiv-Barfi et al. "Therapeutic antitumor immunity by checkpoint blockade is enhanced by ibrutinib, an inhibitor of both BTK and ITK." Proceedings of the National Academy of Sciences 112(9): E966-E972 (2015).
Siurala et al. "Oncolytic adenovirus and doxorubicin-based chemotherapy results in synergistic antitumor activity against soft-tissue sarcoma." International Journal of Cancer 136(4): 945-954 (2015).
Vassilev et al. "Repeated intratumoral administration of ONCOS-102 leads to systemic antitumor CD8+ T-cell response and robust cellular and transcriptional immune activation at tumor site in a patient with ovarian cancer." Oncoimmunology 4(7): e1017702 (2015).
Chen et al. "Oncology meets immunology: the cancer-immunity cycle." Immunity 39(1): 1-10 (2013).
Paz-Ares et al. "Randomised open-label phase I/II study adding ONCOS-102 to pemetrexed/cisplatin in patients with unresectable malignant pleural mesothelioma 24-months analysis of clinical outcomes." Targovax Abstract 462. Retrieved from the internet: URL: https://www.targovax.com/en/wp-content/uploads/sites/2/2019/03/paz-ares-abstract-462-sitc-2021-pdf.pdf. 2021.
Shoushtari et al. "1083P A pilot study of engineered adenovirus ONCOS-102 in combination with pembrolizumab (pembro) in checkpoint inhibitor refractory advanced or unresectable melanoma." Annals of Oncology 32(Suppl_5): S897-S898 (2021).
Kaufman et al. "Oncolytic viruses: a new class of immunotherapy drugs." Nature Reviews Drug Discovery 14(9): 642-662 (2015).
Fessas et al. "A molecular and preclinical comparison of the PD-1-targeted T-cell checkpoint inhibitors nivolumab and pembrolizumab." Seminars in Oncology 44(2): 136-140 (2017).
Shoushtari et al. "Pilot Study of ONCOS-102 and Pembrolizumab: Remodeling of the Tumor Microenvironment and Clinical Outcomes in Anti-PD-1-Resistant Advanced Melanoma." Clinical Cancer Research (2022): OF1-OF10.

A

B

C

D

COMBINING ADENOVIRUS AND CHECKPOINT INHIBITORS FOR TREATING CANCER

CROSS-REFERENCE TO RELATED APPLICATIONS

This application is a continuation under 35 U.S.C. § 120 of co-pending U.S. application Ser. No. 16/330,274 filed Mar. 4, 2019; which is a U.S. National Stage under 35 U.S.C. § 371 of International Application No. PCT/FI2017/050645 filed Sep. 11, 2017, which claims the benefit under 35 U.S.C. § 119(a) of European Application No. 16188301.2 filed Sep. 12, 2016, the contents of which are hereby incorporated by reference in their entireties.

FIELD OF THE INVENTION

The present invention relates to the field of medicine. Specifically, the present invention relates to a novel strategy of using ONCOS-102 adenovirus for the treatment of human cancer in combination with a checkpoint inhibitor or checkpoint inhibitors. Also methods of using this combination of virus and checkpoint inhibitor or checkpoint inhibitors in the treatment of human cancer are disclosed. Other medications in addition to the virus and the checkpoint inhibitor or checkpoint inhibitors can also be included into the treatment protocol.

BACKGROUND OF THE INVENTION

An important part of the immune system is its ability to tell between normal cells in the body and those it sees as "foreign." This lets the immune system attack the foreign cells while leaving the normal cells alone. To do this, it uses "checkpoints"—molecules on certain immune cells that need to be activated (or inactivated) to start an immune response.

Cancer cells sometimes find ways to use these checkpoints to avoid being attacked by the immune system. Immune checkpoint inhibitors are drugs—often made of antibodies—that unleash an immune system attack on cancer cells. They've scored some impressive successes in recent years, particularly in some patients with metastatic melanoma or Hodgkin lymphoma, and are showing promise in clinical trials involving patients with other types of cancer.

Targeting checkpoint proteins is quickly becoming an important part of the treatment for some cancers, such as melanoma and non-small cell lung cancer. Researchers have also found promising early results against a number of other cancer types. Unlike most other cancer drugs, these checkpoint inhibitors seem to be helpful against many different types of cancer.

Virotherapy is a relatively novel treatment approach, which harnesses the natural ability of some viruses to kill the cells in which they proliferate and the ability to spread to neighboring cells, thereby amplifying the therapeutic effect of the initial input dose. In virotherapy the cancer cell transduction and viral replication are carefully controlled by genetic engineering of the viral genome to gain effective and safe tumor eradication. Safe tumor eradication necessitates introduction of various genetic modifications to the adenoviral genome, thereby restraining replication exclusively to tumor cells and eventually obtaining selective eradication of the tumor without side effects to healthy tissue.

Specific deletions on adenoviral key regulatory genes can be utilized to create dysfunctional proteins or the lack of their expression that leads to dependence on a specific genetic feature present in target cells. Partial deletions of E1A result in restricted replication in normal cells but allow replication in target cells, such as cancer cells.

Conditionally replicating viruses featuring a 24 base pair deletion in the CR2 (constant region 2) were created and shown to be potent and selective in the treatment of glioma and breast cancer xenografts (Fueyo et al. 2000; Heise et al. 2000). Their cancer specificity results from the inability of dysfunctional E1A to release E2F1 transcription factor, which leads to the requirement of free E2F1. E2F1 is abundant in cancer cells, where the pRb pathway is most often disrupted (Hanahan and Weinberg 2000).

Clinical and preclinical results have shown that treatment with unarmed oncolytic viruses is not immunostimulatory enough to result in sustained anti-tumoral therapeutic immune responses. In this regard, oncolytic viruses have been armed to be more immunostimulatory. Viruses can be engineered to express highly immunogenic proteins such as granulocyte-macrophage colony-stimulating factor (GM-CSF). When immunogenic proteins are expressed within tumor microenvironment, they are potent stimulators of specific and long-lasting antitumor immunity. Introduction of immunotherapeutic genes into tumor cells and, furthermore, their translation into proteins, leads to the activation of the immune response and to more efficient destruction of tumor cells. The most relevant immune cells in this regard are natural killer cells (NK) and cytotoxic CD8+ T-cells.

ONCOS-102 (Ad5/3-D24-GM-CSF; disclosed in WO 2010/072900) is a serotype 5 adenovirus, comprising a chimeric capsid for enhanced gene delivery to cancer cells and a 24 bp deletion in Rb binding site of E1A region for cancer cell restricted replication. ONCOS-102 is armed with granulocyte-macrophage colony-stimulating factor (GM-CSF) for an enhanced immuno-stimulatory effect. Safety and immunological activity of ONCOS-102 has already been demonstrated in phase 1 clinical study (NCT01598129). In this phase 1 study of the present inventors, local treatment of pleural mesothelioma with ONCOS-102 induced a systemic anti-tumor CD8+ T cell response and infiltration of CD8+ T cells into tumors in the last line refractory malignant pleural mesothelioma patient.

Koski et al. (2010) discloses treating total of 21 patients with advanced solid tumors refractory to standard therapies with ONCOS-102. According to those studies ONCOS-102 seems safe in treating cancer patients. Also promising signs of efficacy were seen.

Some examples of combination therapies utilizing virotherapy together with a check-point inhibitors have been disclosed. WO2014/047350 envisages a recombinant oncolytic virus with a gene encoding an anti-PD-1 antibody inserted in the viral genome. Publication WO 2014/036412 relates to methods of treating melanoma using a herpes simplex virus in combination with an immune checkpoint inhibitor. A phase 1b/3 study of talimogene laherparepvec (T-VEC, under the brand name Imlygic) that is a herpes simplex virus (HSV)-1-based oncolytic immunotherapy designed to selectively replicate in tumors, produce GM-CSF and stimulate antitumor immune responses in melanoma, and pembrolizumab in unresectable stage IIIB-IV melanoma is currently going on.

Publication US 20150086541 discloses a method for decreasing or retarding an increase in the size of a localized or metastatic tumor by using a combination of an immune stimulating cytotoxic gene therapy and immune-checkpoint modulating agent, in conjunction with other therapies, including radiation therapy, chemotherapy, surgery, and immunotherapies.

In treating melanoma, a combined approach, wherein treatments target two different checkpoint inhibitors, has been shown to work better than using either treatment alone. However, the combination comes with an increased risk of serious side effects. A further need exists for combination therapies to improve efficacy and safety of treatments directed to inducing immune response against various cancers. Thus, there is a need for additional cancer treatments, especially for advanced melanoma.

SUMMARY OF THE INVENTION

Traditionally, it has been considered that virus presence in the lesions is needed for its efficacy. Now the inventors have surprisingly found a systemic effect that is produced by the virus even though virus is administered locally. It was also surprising that after an intense priming period with ONCOS-102, the originally PD-1 inhibitor refractory tumors become sensitive to PD-1 inhibitors.

Objects of the present invention are to provide a novel combination of oncolytic adenovirus and a checkpoint inhibitor or checkpoint inhibitors, a novel combination therapy using oncolytic adenovirus and checkpoint inhibitor or checkpoint inhibitors for treating cancer in a patient and also to solve problems relating to conventional cancer therapy.

One aspect of the invention is ONCOS-102 adenovirus for use in the treatment of human cancer, preferably in the treatment of human malignant melanoma, wherein administering the virus to a human patient in need thereof is done in combination with administering a checkpoint inhibitor or checkpoint inhibitors.

Another aspect of the invention is a method for treating human cancer, preferably human malignant melanoma, in a patient comprising a step of administering to said patient ONCOS-102 adenovirus and a checkpoint inhibitor or checkpoint inhibitors.

Still another aspect of the invention is the use of ONCOS-102 adenovirus in the treatment of human melanoma, wherein the virus is administered to a patient in combination with a checkpoint inhibitor or checkpoint inhibitors.

BRIEF DESCRIPTION OF THE DRAWINGS

The following figure is included to further demonstrate certain aspects and features of the present invention. The invention may be better understood by reference to one or more of these drawings in combination with the detailed description of specific embodiments, including examples.

DETAILED DESCRIPTION OF THE INVENTION

Figure 1:
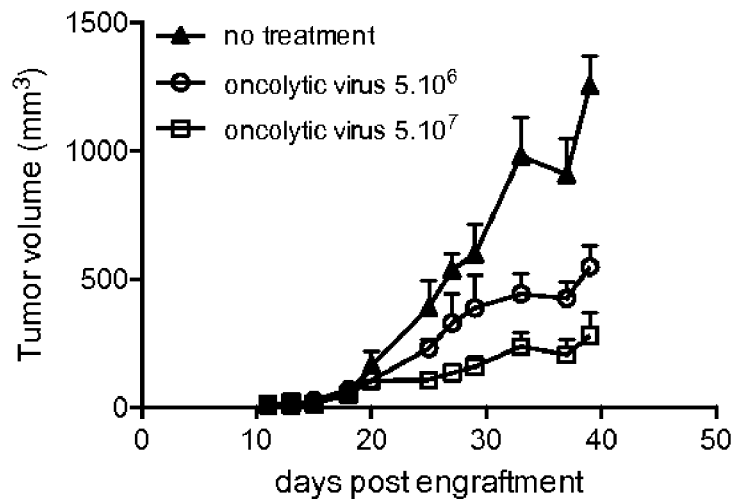
FIG. 1. Treatment of human melanoma A-375 cell based tumors in immunodeficient and humanized mice with ONCOS-102 alone, with checkpoint inhibitor alone or with checkpoint inhibitor in combination with ONCOS-102, in an efficacy study. A) A-375 cell based tumor shows virus-dose dependent sensitivity in immunodeficient mice. B) Human immune system inhibits A-375 tumor growth in humanized mice, while tumor growth is not inhibited in untreated immunodeficient mice. C) Systemic effect of Oncolytic virus in combination with pembrolizumab (Keytruda) in humanized NOG mice engrafted with A375 tumor cells is shown. The growth of both the right SK-MEL2 tumor treated with ONCOS-102 ($5 \times 10^7$ VP) and the growth of left SK-MEL2 tumor not treated with ONCOS-102 are similarly inhibited, as compared to the tumor treated with pembrolizumab only. The tumor in mice, wherein only pembrolizumab is administered as an IP injection (Keytruda), showed no reduction in the growth rate further illustrating that the presence of ONCOS-102 is needed for the systemic effect. D) The combination of pembrolizumab (Keytruda) with ONCOS-102 shows enhanced antitumor effect towards A-375 tumor in humanized mice as compared to treating the mice with ONCOS-102, pembrolizumb or nivolumab (Opdivo) only.
Figure 1:
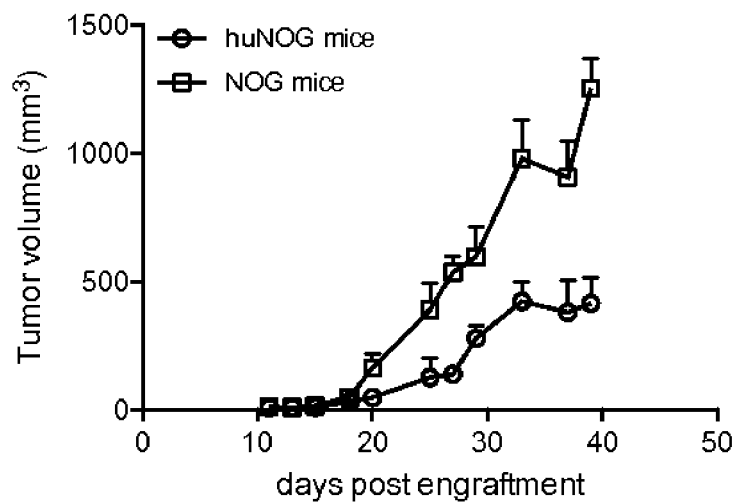
Figure 1:
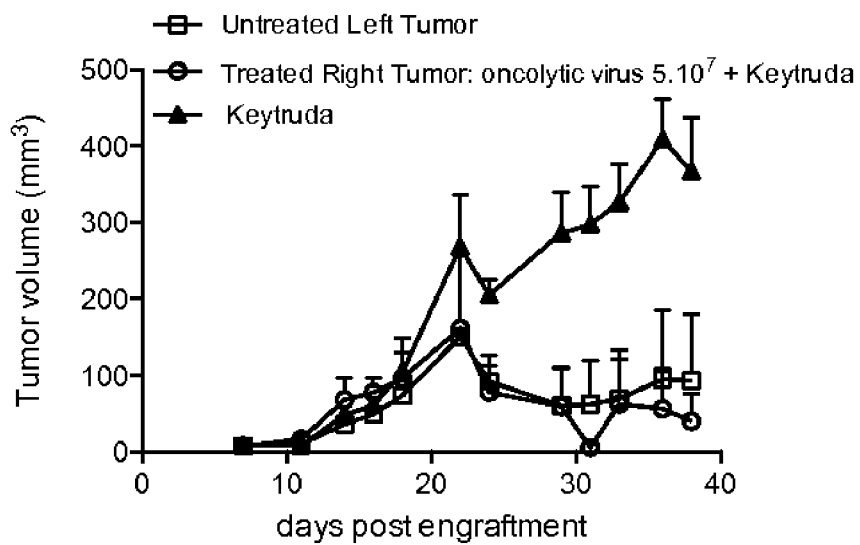
Figure 1:
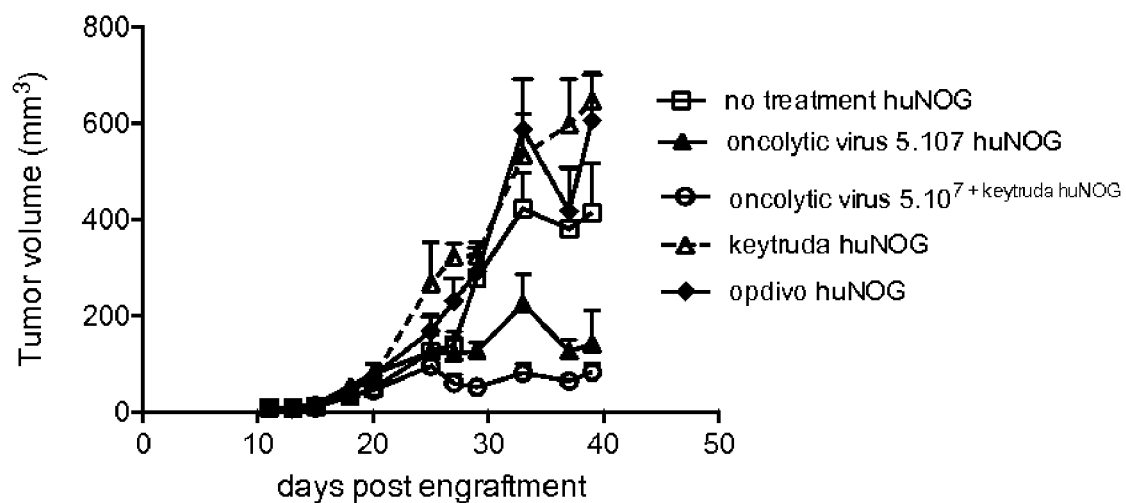

Unless defined otherwise, all technical and scientific terms used in this application have the same meaning as commonly understood by one of ordinary skill in the art to which this invention pertains.

The term "anti-viral response" as used herein refers to a cell's response to viral infection and includes, for example, production of interferons, cytokine release, production of chemokines, production of lymphokines or any combination thereof.

The expressions "normal host cell" and "normal tissue" as used herein refer to a non-cancerous, non-infected cell or tissue with an intact anti-viral response.

The term "oncolytic agent" as used herein refers to an agent capable of inhibiting the growth of and/or killing tumor cells.

The term "subject" as used herein refers to any living organism, including humans and animals, human and animal tissue, and human and animal cells.

The term "patient" as used herein refers to any subject (preferably human) afflicted with a disease, such as melanoma, who is likely to benefit from a treatment with combination therapy as described herein.

Adenoviruses are non-enveloped viruses 70-90 nm in diameter with an icosahedral capsid. Their genome is linear, double stranded DNA varying between 25-45 kilobases in size with inverted terminal repeats (ITRs) at both termini and a terminal protein attached to the 5' ends.

The icosahedral capsid is formed by three major proteins, of which the hexon trimers are most abundant. Each of the twelve vertices of the capsid also contains a pentameric protein, a penton base that is covalently attached to the fiber. The fiber is a trimeric protein that protrudes from the penton base and is a knobbed rod-like structure. Other viral proteins IIIc, IVa2, VI, VIII and IX are also associated with the viral capsid. The proteins VII, small peptide mu and a terminal protein (TP) are associated with DNA. Protein V provides a structural link to the capsid via protein VI.

As used herein the term "capsid" refers to the protein shell of the virus, which includes hexon, fiber and penton base proteins.

All human adenoviruses have similarities in their fiber architecture. Each has an N-terminal tail, a shaft with repeating sequences, and a C-terminal knob domain with a globular structure. The knob domain is principally responsible for binding the target cellular receptor and its globular structure presents a large surface for lateral and apical binding. The fiber proteins of adenoviruses from different subgroups most distinctively differ in length and ability to bend.

The fiber participates in attachment of the virus to the target cell. First, the knob domain of the fiber protein binds to the receptor of the target cell, secondly, the virus interacts with an integrin molecule, and thirdly, the virus is endocytosed into the target cell. Next, the viral genome is transported from endosomes into the nucleus and the replication of the viral genome can begin.

As used herein, "Ad5/3 chimerism" of the capsid refers to a chimerism, wherein the knob part of the fiber is from Ad serotype 3, and the rest of the fiber is from Ad serotype 5.

Adenoviruses are dependent on the cellular machinery to replicate the viral genome. They can infect quiescent cells and induce them into a cell cycle S-phase-like state enabling viral DNA replication. The adenoviral genome can be divided into immediate early (E1A), early (E1B, E2, E3, E4), intermediate (IX, Iva), and late (L1-L5) genes.

E3 gene products are not essential for virus replication in vitro, but are dedicated to the control of various host immune responses. E3-gp19K inhibits the transport of the class 1 major histocompatibility complex (MHC) from the endoplasmic reticulum (ER) to the plasma membrane, thereby preventing the presentation of peptides to T lymphocytes by MHC.

The adenoviral E1A protein was originally described as a pRb binding protein capable of inducing DNA replication in quiescent normal cells. One of the key functions of E1A protein is to disrupt the pRb-E2F interactions, thereby releasing E2F transcription factors to activate the E2F responsive promoters and transcription of the genes they control, such as adenoviral E2A. The conserved region 2 (CR2) in E1A protein forms a strong interaction with the pocket binding domain of pRb and CR1 mediates the actual disruption of the E2F binding of pRb. Conditionally replicating viruses featuring a 24 base pair deletion in the CR2 were created and shown to be potent and selective in the treatment of glioma and breast cancer xenografts. Their cancer specificity results from the inability of dysfunctional E1A to release E2F1 transcription factor, which leads to the requirement of free E2F1.

ONCOS-102 adenovirus has been earlier disclosed in publication WO 2010/072900. ONCOS-102 is a serotype 5 adenovirus (Ad5) displaying the following modifications differing from the Ad5 genome:
1. A 24 base pair (bp) deletion in the E1A-gene constant region 2 (CR2). The dysfunctional E1A protein is unable to bind and release E2F1 transcription factor from the retinoblastoma protein (Rb), leading to the requirement of free E2F1 for adenovirus gene transcription. Free E2F1 is abundant in cancer cells, where the pRb pathway is most often disrupted. Thereby viruses with the 24 bp deletion in E1A are able to efficiently replicate in cancer cells. The E1A gene transcription into mRNA is being controlled by the endogenous E1A promoter.
2. A 965 bp deletion has been introduced in the early 3 (E3) region coding for 6.7K and gp19K proteins. These proteins are associated with the ability of adenovirus to evade host immune control mechanisms and their functions are expendable for adenoviral replication.
3. A transgene coding for the human granulocyte macrophage colony stimulating factor (GM-CSF) protein has been inserted to the E3 region, replacing 6.7K and gp19K. The GM-CSF gene transcription into mRNA is being controlled by the endogenous E3 promoter. In other words, in ONCOS-102 adenovirus 965 base pairs coding for the viral genes gp19K and 6.7K have been deleted from the E3 region and a transgene GM-CSF has been introduced to replace them.
4. The serotype 5 fiber knob has been replaced by serotype 3 fiber, thereby allowing entry of the virus to cells via the serotype 3 receptor instead of the serotype 5 receptor CAR.

In ONCOS-102 adenovirus the native E1A promoter is present, i.e. it has not been replaced by another promoter.

In short, in ONCOS-102 adenovirus, GM-CSF is under endogenous viral E3 control elements, which results in replication-associated transgene expression starting about 8 hours after infection. The virus replicates in a tumor-selective manner thus resulting in tumor-restricted production of GM-CSF. Tumor specificity is achieved by a 24-bp deletion, which abrogates the Rb-binding site of E1A and, as demonstrated in previous reports, the virus replicates selectively in cells with p16-Rb pathway defects, including most if not all human cancers. The oncolytic potency of ONCOS-102 adenovirus was shown to be more effective than the wild-type control virus.

Oncolytic adenoviruses that express GM-CSF induce anti-cancer immunity while acting directly on cancer cells by oncolysis. GM-CSF is a potent inducer of systemic anti-tumor immunity associated with recruitment and maturation of antigen presenting cells (APCs), mainly dendritic cells, as well as recruitment of cells of the innate immunity arm. However, systemically elevated cytokine levels represent a risk for toxic side-effects. Besides the direct risk of side effects mediated by high serums concentrations of GM-CSF, an indirect risk results from recruitment of myeloid derived suppressor cells (MDSC). While the immunosuppressive effect of MDSC is potentially harmful for cancer patients in general, it could be particularly counterproductive in the context of cancer immunotherapy. Thus restricting the GM-CSF expression to the tumor site is crucial.

ONCOS-102 adenovirus has shown a good oncolytic potential and production of functionally active human GM-CSF in vitro (Koski et al. 2010). It was shown in immune-competent hamsters that the virus is effective in deterring the growth of aggressive syngeneic pancreatic tumors. Evidence of replication of the virus in tumors was shown by measuring viral copy number. Selectivity of replication was demonstrated as there was no increase in viral copy numbers in directly injected liver tissue. Local replication-linked production of GM-CSF in tumors was demonstrated, while there was very little leakage of GM-CSF into serum or liver. It was also shown that combining low-dose cyclophosphamide with ONCOS-102 adenovirus can enhance antitumor effect, whereas cyclophosphamide treatment alone did not result in significant reduction of tumor growth.

Overall, treatment of advanced cancer patients with ONCOS-102 adenovirus appears to be safe and promising signs of possible efficacy have been observed. Although virus is present in serum for extended periods even after a single dose, multiple injections are likely to improve tumor transduction and enhance antitumor immunity.

As used herein, the term "immune checkpoint inhibitor" or "checkpoint inhibitor" refers to molecules that totally or partially reduce, inhibit, interfere with or modulate one or more checkpoint proteins. Checkpoint proteins regulate T-cell activation or function. Central to the immune checkpoint process are the cytotoxic T-lymphocyte-associated antigen 4 (CTLA-4) and programmed death 1 (PD-1) immune checkpoint pathways. The CTLA-4 and PD-1 pathways are thought to operate at different stages of an immune response. CTLA-4 is considered the "leader" of the immune checkpoint inhibitors, as it stops potentially autoreactive T cells at the initial stage of naive T-cell activation, typically in lymph nodes. The PD-1 pathway regulates previously activated T cells at the later stages of an immune response, primarily in peripheral tissues.

Progressing patients have been shown to lack of PD-L1 upregulation by either tumor cells or tumor-infiltrating immune cells (Romano et al. 2015). Immune therapies targeting the PD-L1/PD-1 pathway might thus be especially effective in tumors where this immune suppressive axis is operational, and reversing the balance towards an immune protective environment would rekindle and strengthen a pre-existing anti-tumor immune response. Monoclonal antibodies can block cellular interactions that negatively regulate T-cell immune responses, such as CD80/CTLA-4 and PD-1/PD-1L, amplifying preexisting immunity and thereby evoking antitumor immune responses (Sagiv-Barfi et al. 2015).

PD-1 thus limits the activity of T cells in peripheral tissues at the time of an inflammatory response to infection and to limit autoimmunity PD-1 blockade in vitro enhances T-cell proliferation and cytokine production in response to a challenge by specific antigen targets or by allogeneic cells in mixed lymphocyte reactions. PD-1 blockade can be accomplished by a variety of mechanisms including antibodies that bind PD-1 or its ligand, PD-L1.

Inhibition of the immune checkpoint pathways has led to the approval of several new drugs: ipilimumab (anti-CTLA-4; Yervoy®), pembrolizumab (anti-PD-1; Keytruda®), and nivolumab (anti-PD-1; Opdivo®). Also PD-L1 inhibitors, such as Atezolizumab (MPDL3280), Avelumab (MSB0010718C) and Durvalumab (MEDI4736), are available. These antagonistic antibodies have been associated with objective clinical responses in cancer patients. Antibodies targeting CTLA-4 are already marketed (e.g. Ipilimumab, Yervoy, Bristol-Myers Squibb, BMS) for metastatic melanoma. Antibody therapies with anti PD-L1 (e.g. MPDL3280A, Roche), anti PD-1 (e.g. Nivolumab, BMS) are also ongoing.

Other immune-checkpoint inhibitors include lymphocyte activation gene-3 (LAG-3) inhibitors, such as IMP321, a soluble Ig fusion protein. Other immune-checkpoint inhibitors include B7 inhibitors, such as B7-H3 and B7-H4 inhibitors. In particular, the anti-B7-H3 antibody MGA271. Also included are TIM3 (T-cell immunoglobulin domain and mucin domain 3) inhibitors.

In certain embodiments the PD-1 blockers include anti-PD-L1 antibodies. In certain other embodiments the PD-1 blockers include anti-PD-1 antibodies and similar binding proteins such as nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD-1; AMP-224 is a fusion protein of B7-DC; an antibody Fc portion; BMS-936559 (MDX-1105-01) for PD-L1 (B7-H1) blockade. Further examples of PD-L1 inhibitors that can be used in certain embodiments are Atezolizumab (MPDL3280), Avelumab (MSB0010718C) and Durvalumab.

Preferably, anti-PD-1 antibodies pembrolizumab (Keytruda), and nivolumab (Opdivo) are used in the invention. Also PD-L1 inhibitors, such as durvalumab can be used in combination with anti-PD-1-antibodies. The preferred checkpoint inhibitors of the present invention are thus those for PD-1 and PD-L1.

Pembrolizumab (Keytruda) and nivolumab (Opdivo) have been shown to be helpful in treating several types of cancer, including melanoma of the skin, non-small cell lung cancer, kidney cancer, head and neck cancers, and Hodgkin lymphoma. They are also being studied for use against many other types of cancer. A phase 1B clinical trial of durvalumab and tremelimumab (monoclonal antibodies targeting PD-L1) have shown some activity in non-small cell lung cancer (NSCLC). Phase 1 data in advanced metastatic urothelial bladder (Study 1108) has led to FDA breakthrough therapy designation. Further, early results of a phase I trial combining durvalumab and gefitinib in lung cancer patients have "showed promise". Further example of a drug that targets PD-L1 is Atezolizumab (Tecentriq). This drug can be used to treat bladder cancer, and is also being studied for use against other types of cancer.

Cancer types that can be treated by the method of the invention utilizing ONCOS-102 in combination with one or more checkpoint inhibitors are for example melanoma, renal cancer, ovarian cancer, bladder cancer prostate cancer, breast cancer, colorectal cancer, lung cancer (such as small-cell lung carcinoma, non-small-cell lung carcinoma and squamous non-small-cell lung carcinoma), gastric cancer, classical Hodgkin lymphoma, mesothelioma, and liver cancer. Preferably, the cancer to be treated with the present invention is advanced melanoma.

Melanoma is a tumor of melanocytes, cells that are derived from the neural crest. Melanoma occurs predominantly in adults, and more than half of the cases arise in apparently normal areas of the skin. Although most melanomas arise in the skin, they may also arise from mucosal surfaces or at other sites to which neural crest cells migrate. "Malignant melanoma" or "melanoma" as used herein refers to a type of cancer that develops from the pigment-containing cells known as melanocytes. Melanomas typically occur in the skin but may rarely occur in the mouth, intestines, or eye. When melanoma spreads to other places in the body, it's called metastatic, or advanced. Thus, "advanced melanoma" as used herein refers to metastatic melanoma. The advanced melanoma is the principal target of the combination therapy as described herein.

Melanoma patient's prognosis is affected by clinical and histological factors and by anatomic location of the lesion. Thickness and/or level of invasion of the melanoma, tumor infiltrating lymphocytes, mitotic index, and ulceration or bleeding at the primary site affect the prognosis. Clinical staging is based on whether the tumor has spread to regional lymph nodes or distant sites. Melanoma can spread by local extension (through lymphatics) and/or by hematological routes to distant sites. Any organ may be involved by metastases, but lungs and liver are common sites.

Stage IV melanomas (i.e. advanced melanomas) are often hard to cure, as they have already spread to distant lymph nodes or other areas of the body. Traditional nonsurgical therapies for unresectable or advanced melanoma in adults include, chemotherapy (Dacarbazine, temozolomide, or other agents either alone or in combination), or interleukin-2. Although some regimes produced objective responses, they were usually short-lived. Newer therapies such as BRAF inhibition (vemurafenib) and immune stimulatory agents (ipilimumab) have shown significant improvement in overall survival compared to control treatments for a limited percentage of patients treated, however toxicity is an issue.

The treatment of advanced melanomas has changed in recent years as newer forms of immunotherapy and targeted drugs have been shown to be more effective than chemotherapy. Current immunotherapy approaches for melanoma fall into seven main categories: checkpoint inhibitors, oncolytic virus therapies, cancer vaccines, adjuvant immunotherapy, adoptive cell therapy, monoclonal antibodies, and cytokines. A core concept in cancer immunotherapy is that tumor cells, which would normally be recognized by T cells, have developed ways to evade the host immune system by taking advantage of peripheral tolerance. Checkpoint inhibitors such as pembrolizumab (Keytruda), nivolumab (Opdivo), and ipilimumab (Yervoy) have been shown to help some people with advanced melanoma live longer.

"Chemotherapy" as used herein refers to the use of chemical compounds or drugs in the treatment of disease, though the term chemotherapy is most often associated with the treatment of cancer. Cancer chemotherapeutic compounds encompass nearly 100 individual drugs.

As disclosed earlier, cancer therapy with ONCOS-102 adenovirus as well as therapy with a checkpoint inhibitor has shown some efficacy when used alone. The inventors wanted to study whether the combination of adenoviral gene therapy with checkpoint inhibitors might be more effective in the treatment of advanced melanoma than either one alone. Particularly, the present inventors were interested whether advanced melanoma, which has stopped responding to prior treatment with checkpoint inhibitor, will start responding again if treated with ONCOS-102.

"Combination therapy" as used herein refers to administration of ONCOS-102 and a checkpoint inhibitor or checkpoint inhibitors that are administered to a patient in need thereof. Preferably, ONCOS-102 is used in combination with an anti-PD-1 antibody, such as pembrolizumab. Also a combination of ONCOS-102 and two anti-PD-1 antibodies, a combination of anti-PD-1 antibody and anti-PD-L1 antibody or two anti-PD-L1 antibodies can be administered to a patient in the need thereof.

In previous studies, it has occurred that some patients acquired resistance to PD-1 inhibitor treatment. Likely the problem is that there is no underlying immunity against the tumor, in which case checkpoint inhibitors are ineffective as they decrease immune suppression but do not generate immunity.

The present inventors have earlier shown that ONCOS-102 induced tumor specific T cell response (CD8+ T cells in peripheral blood) in patients from which tumor specific T cell responses could not be detected before the treatment (Ranki et al 2014, Ranki et al. 2016 and Vassilev et al. 2015). Further, a dynamic adaptive change in cancer cells depicted in the form of PD-L1 up-regulation after treatment was seen, thus suggesting that ONCOS-102 might help to prime the tumors to be responsive to the checkpoint inhibitors, such as PD-1/PD-L1 inhibitors.

In the combination therapy the virus and also the checkpoint inhibitor or inhibitors may be administered in several doses during several days. The treatment protocol comprises first priming with the virus followed by administering the checkpoint inhibitor and then optionally continuing administration of both the virus and checkpoint inhibitor. Also reverse sequence of administrations can be used, i.e. first priming with the checkpoint inhibitor or inhibitors followed by administering the virus and then optionally continuing administration of both the virus and checkpoint inhibitor.

The term "priming" as used herein refers for example to administering oncolytic virus first to sensitize the cells to the effects of checkpoint inhibitors. Also checkpoint inhibitors can be used to sensitize the cells before administering the virus. "Priming" can also refer to using of apoptosis-inducing pretreatment. The tumor priming done with oncolytic viruses results in immunogenic cancer cell death, which is associated with the presentation of calreticulin on the cell surface and the release of natural adjuvants, specifically high-mobility group protein B1 (HMGB1) and ATP from within the dying cells, eventually leading to DC stimulation and subsequent activation of adaptive immune response. This virus-induced change in the tumor environment is essential in priming a meaningful antitumor immune response. Antigen presenting cells capture tumor antigens from dying tumor cells and process them for MHC class I and II presentation, migrate to draining lymph nodes and stimulate antigen-specific B and T cells.

"Virus sensitizer" as used herein refers to an agent that can improve oncolytic virus efficacy. Agents suitable for such combination therapy or which can be used as virus sensitizers include but are not limited to All-trans retinoic acid, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, erlotinib, Etoposide, Fluorouracil, Gemcitabine, Hydroxyurea, Idarubicin, Imatinib, Mechlorethamine, Mercaptopurine, Methotrexate, Mitoxantrone, Oxaliplatin, Paclitaxel, Pemetrexed, Temozolomide, Teniposide, Tioguanine, Valrubicin, Vinblastine, Vincristine, Vindesine and Vinorelbine. Preferably, the virus sensitizer to be used is cyclophosphamide.

As used herein "concurrent" refers to a medication or therapy, which has been administered before, after or simultaneously with the combination therapy as described herein. The period for a concurrent therapy may vary from minutes to several weeks. Typically, the therapy that is concurrent with the combination therapy as described herein lasts for some days or some weeks.

As used herein, the term "effective amount" refers to an amount of a compound, therapeutic agent, virus or drug, which is capable of performing the intended result. For example, an effective amount of a checkpoint inhibitor and/or adenovirus is an amount sufficient to effect beneficial or desired clinical results including clinical results. An effective amount can be administered in one or more administrations. As described herein, the effective amount is an amount sufficient to ameliorate, stabilize, reverse, slow and/or delay progression of malignant melanoma or to cure malignant melanoma. In the present invention, the effect of a checkpoint inhibitor and ONCOS-102 adenovirus can be monitored for example by monitoring tumor reaction to said treatment. Monitoring of the tumor reaction may be performed with any suitable method known in the art. It can be performed for example with methods measuring immunologic status of the cells, such as those listed in Ranki et al. (2014). For example, monitoring can be done by measuring the presence of tumor infiltrating lymphocytes in the tumor, TH1-type response can be monitored with a microarray, and also IFNγ enzyme linked immunospot assay (ELISPOT) can be utilized in monitoring.

The effective amount is thus such that is capable to or required to cause a desired effect or reaction in the tumor. As is understood in the art, an effective amount may vary, depending on, inter alia, patient history as well as other factors such as the type and/or dosage of a checkpoint inhibitor used.

As used herein, the term "treatment period" refers to a time period when the combination treatment is conducted. Treatment period may consist of several administrations of ONCOS-102 and checkpoint inhibitor, wherein the administrations can be performed in cycles. Treatment period can last weeks or months. Treatment period can last up to one year.

As used herein, the term "administration period" refers to a time period the adenovirus, the checkpoint inhibitors, or other medication are administered to a patient. During the administration period a single dose or several doses of the agent in question can be administered. The administration period can be minutes, hours, days, weeks or months. The administration period can consist of cycles. For example, a three-week (21 days) cycle can be used in the administration of the checkpoint inhibitor or checkpoint inhibitors.

Pembrolizumab (Keytruda) is usually administered as one dose in three weeks, but also other cycles, such as administering a reduced amount every week can be used. Nivolumab (Opdivo) is usually administered as one dose per two weeks, but also other cycles, such as administering a reduced amount every week can be used.

Therapeutic compositions are generally formulated relative to the particular administration route. In the combination therapy as described herein checkpoint inhibitor, such as pembrolizumab, is used in its effective concentration. As an example, pembrolizumab can be administered as an intravenous (i.v.) infusion over 10 minutes on Day 1 of each 21-day cycle, when 21-day cycle is used.

Another object of the present invention is ONCOS-102 adenovirus for use in the treatment of human melanoma, especially advanced human melanoma, wherein the virus is administered in combination with checkpoint inhibitor to a patient, and wherein the checkpoint inhibitor is pembrolizumab.

In some embodiments of the present invention, various combinations of Cyclohexamide, Cyanocobolamine, Folatic acid and Dexamethasone can also be used in addition to ONCOS-102 and a checkpoint inhibitor or inhibitors. More specifically, from the list of agents consisting of Cyclohexamide, Cyanocobolamine, Folatic acid and Dexamethasone, one, two, three or four and any combination thereof can be used concurrently with the combination therapy comprising ONCOS-102 and a checkpoint inhibitor. As an example, the subject can be treated with one or more adjunctive agents that reduce or eliminate hypersensitivity reactions before, during, and after administration of the agents of the combination therapy described, such as one or more of dexamethasone, folic acid, and Vitamin B12 before, during, and after administration of the agents of the combination therapy. In certain embodiments, the subject is treated with 2-25 mg of dexamethasone orally on the day before, the day of, and the day after administration of the agents of the combination therapy; 400-1000 µg of folic acid orally daily, during a period starting 7 days before administration of the agents of the combination therapy, throughout at least one treatment period, and for 21 days after the last administration of agents of the combination therapy; and 1000 µg of Vitamin B12 intramuscularly 1 week before the first administration of agents of the combination therapy in a treatment period.

Any conventional method may be used for administration of ONCOS-102 to a patient in need thereof. The route of administration depends on the formulation or form of the composition, the disease, location of tumors, the patient, comorbidities and other factors. In a preferred embodiment of the invention, the administration is conducted through an intratumoral, intramuscular, intra-arterial, intrapleural, intra-vesicular, intracavitary or peritoneal injection, or an oral administration. Preferably, the administration is conducted as intratumoral injection or intraperitoneal injection.

The injection can be personalized for each patient according to the location and size of tumors. For example, the virus can be injected (i.t.) in a volume from 0.5 ml to 10 ml. The injection can be done to several, preferably up to five, different tumor sites. The volume of intraperitoneal dosage can vary from 200 ml to 800 ml. Preferably, the administered volume is 500 ml.

The effective dose of vectors depends on at least the subject in need of the treatment, tumor type, location of the tumor and stage of the tumor. The dose may vary for example from about $10^8$ viral particles (VP) to about $10^{14}$ VP, preferably from about $5\times10^9$ VP to about $10^{13}$ VP and more preferably from about $8\times10^9$ VP to about $10^{12}$ VP. In one specific embodiment of the invention the dose is in the range of about $5\times10^{10}$-$5\times10^{11}$ VP. Thus, the amount of ONCOS-102 adenovirus to be administered can be in the range of $5\times10^{10}$-$5\times10^{11}$ VP. Preferably, ONCOS-102 is administered at $3\times10^{11}$ VP. On the other hand, expressed in the plaque forming units, ONCOS-102 can be administered by direct injection into tumor, such as advanced melanoma tumor, of said patient or intraperitoneally at a dose of about $10^8$-$10^{12}$ plaque forming units.

One object of the invention is ONCOS-102 adenovirus for use in the treatment of human cancer, such as advanced melanoma, wherein the virus is administered in combination with a checkpoint inhibitor, such as pembrolizumab, to a patient in need thereof, and wherein the amount of the virus is from $5\times10^{10}$ to $5\times10^{11}$ VP.

Another object of the invention is ONCOS-102 adenovirus for use in the treatment of human cancer, such as advanced melanoma, wherein the virus is administered in combination a checkpoint inhibitor to a patient, and wherein the virus is administered in an amount of $3\times10^{11}$ VP/5 ml.

A further aspect of the invention is ONCOS-102 adenovirus for use in the treatment of human cancer, such as advanced melanoma, wherein the virus is administered in combination with a checkpoint inhibitor to a patient, and wherein the checkpoint inhibitor and the virus are administered in effective amounts.

Still another object of the invention is ONCOS-102 adenovirus for use in the treatment of human cancer, such as advanced melanoma, wherein the virus is administered in combination a checkpoint inhibitor to a patient in need thereof, and wherein the virus is administered intraperitoneally or by direct injection into tumor and the check-point inhibitor or inhibitors are administered intravenously or intraperitoneally.

According to one aspect of the invention ONCOS-102 adenovirus is for use in the treatment of human cancer, such as advanced melanoma, wherein the virus is administered in combination with a checkpoint inhibitor to a patient in need thereof, and wherein the virus is administered before administering of the checkpoint inhibitor or inhibitors and also during administering period of said a checkpoint inhibitor or inhibitors.

According to one preferred embodiment the agents of the combination therapy may be administered with first priming with administering the virus in one dose or from one to ten times during a one-day to ten-month period and then administering a checkpoint inhibitor for example from one to four weeks after starting the virus administration. The administration may for example be in the following sequential order: Priming with the virus is done by administering the virus to the subject in need three times during 8 days (days 1, 4, 8) and pembrolizumab (Keytruda) is then administered on day 21 and onwards three weekly. The administration of the checkpoint inhibitor, preferably pembrolizumab, can be thus started after three weeks of starting the administration of the virus. The administration of checkpoint inhibitor or inhibitors can be continued so that the administration is for example done a total of six times in about three-week cycles. The administration times can vary from one to six times.

The oncolytic adenoviral vector of the invention induces virion-mediated oncolysis of tumor cells and activates human immune response against tumor cells. In a preferred embodiment of the invention, the method or use further comprises administration of substances capable of downregulating regulatory T-cells in a subject. "Substances capable of downregulating regulatory T-cells" refers to agents that reduce the amount of cells identified as T-suppressor or Regulatory T-cells. These cells have been identified as consisting one or many of the following immunophenotypic markers: CD4+, CD25+, FoxP3+, CD127− and GITR+. Such agents reducing T-suppressor or Regulatory T-cells may be selected from a group consisting of anti-CD25 antibodies or chemotherapeutics.

The immunomodulatory functions of the transgene GM-CSF are a central mechanism of action of armed oncolytic adenoviruses and in addition, adenovirus itself is a strong activator of the immune system and this significantly contributes to the overall anti-tumor efficacy of the virus.

Another aspect of the present invention is a method for treating human cancer, such as advanced malignant melanoma, in a patient comprising a step of administering to said patient ONCOS-102 adenovirus and a checkpoint inhibitor in amounts and for a time sufficient to kill cancer cells or to prevent the growth of cancer cells.

One preferred aspect of the invention is a method for treating human cancer, such as advanced malignant melanoma, in a patient comprising a step of administering to said patient ONCOS-102 adenovirus and a checkpoint inhibitor or inhibitors, wherein the treatment comprises administering checkpoint inhibitor pembrolizumab.

Another preferred aspect of the invention is a method for treating human cancer, such as advanced melanoma, in a patient comprising the steps of administering to said patient ONCOS-102 adenovirus and a checkpoint inhibitor or checkpoint inhibitors, wherein said virus is first administered before starting the administration period of the checkpoint inhibitor or checkpoint inhibitors and the virus can also be administered during the administration period of said check-point inhibitor or inhibitors.

Still another preferred aspect of the invention is a method for treating human cancer, such as advanced melanoma, in a patient comprising the steps of administering to said patient ONCOS-102 adenovirus and a checkpoint inhibitor or checkpoint inhibitors, wherein ONCOS-102 adenovirus is administered from one to ten times and a checkpoint inhibitor or inhibitors is/are administered from one to six times to said patient.

Still another preferred aspect of the invention is a method for treating human cancer, such as advanced melanoma, in a patient comprising the steps of administering to said patient ONCOS-102 adenovirus and a checkpoint inhibitor or checkpoint inhibitors, wherein the amount of ONCOS-102 adenovirus to be administered is in the range of $5\times10^{10}$-$5\times10^{11}$ VP.

Still another preferred aspect of the invention is a method for treating human cancer, such as advanced melanoma, in a patient comprising the steps of administering to said patient ONCOS-102 adenovirus and a checkpoint inhibitor or checkpoint inhibitors, wherein said checkpoint inhibitors are administered as: pembrolizumab (Keytruda) 2 mg/kg every three weeks, nivolumab (Opdivo) 2 mg/mg every two weeks and durvalumab 20 mg/kg every four weeks or 10 mg/kg every two weeks. Durvalumab can be administered by IV infusion once every four weeks for a total of 12 four-week cycles.

A further aspect of the invention is a use of ONCOS-102 adenovirus in the treatment of human cancer, such as advanced malignant melanoma, wherein the virus is administered to a patient in combination with a checkpoint inhibitor or checkpoint inhibitors.

Still a further aspect of the invention is ONCOS-102 adenovirus for use in the treatment of human cancer, such as advanced melanoma, wherein the virus is administered in combination with one, two or three checkpoint inhibitors to a patient in need thereof.

Still a further aspect of the invention is ONCOS-102 adenovirus for use in the treatment of human cancer, such as advanced melanoma, wherein ONCOS-102 adenovirus is administered from one to ten times and the checkpoint inhibitor is administered from 1 to 15 times to a patient in need thereof.

Concurrent administration of cyclophosphamide (CPO) to the patient can be done during the time period of combination therapy. Cyclophosphamide is a common chemotherapeutic agent, which has also been used in some autoimmune disorders. Cyclophosphamide has been shown to improve oncolytic virus efficacy through several mechanisms. It dampens the innate antiviral response, slows the generation of anti-oncolytic virus neutralizing antibodies, may target T-regs and may affect tumor vasculature enhancing oncolytic virus extravasation. Several preclinical studies have shown that cyclophosphamide can retard immune clearance of oncolytic viruses, enhance persistence of virus infection and prolong therapeutic efficacy. In the present invention, cyclophosphamide can be used as a virus sensitizer to enhance viral replication and the effects of GM-CSF induced stimulation of NK and cytotoxic T-cells for enhanced immune response against the tumor. It can be used as intravenous bolus doses or low-dose oral metronomic administration. Other suitable virus sensitizers that can be used in embodiments of the present invention include temozolomide and erlotinib.

To reduce regulatory T cells, the patients will receive low dose CPO, one to four days before the first injection of ONCOS-102. CPO will be administered for example as an i.v. bolus of 300 mg/m$^2$. The bolus may vary between 100 and 600 mg/m$^2$. The route of administration of CPO can also be for example oral administration. Also metronomic chemotherapy may be used.

Also Folic acid can be administered to the patient before start of the combination therapy and also during the combination therapy. The administration of Folic acid can be started at least five days before administration of first dose of chemotherapeutic agents of the combination therapy. For example, the administration can be started 1-2 weeks before starting the administration of the agents of the combination therapy. Folic acid can be administered daily (oral administration; PO) and the administration can be continued also during the combination therapy. The administration can be continued until about three weeks after last dose of the agents of the combination therapy. The typical dose of Folic acid is 4 mg (PO). One preferred aspect of the invention is a method for treatment of melanoma in a patient in need thereof comprising the steps of (a) administering to said patient ONCOS-102 adenovirus and a checkpoint inhibitor and a step of administration of Folic acid to the patient.

Cyanocobolamin (Vitamin B12) can be administered to the patient before start of the combination therapy and also during the combination therapy. The administration of Cyanocobolamin is typically started 1-2 weeks before starting the administration of the agents of the combination therapy. Cyanocobolamin can be administered for example as intramuscular injection (i.m.) on nine-week intervals and also during the combination therapy. The administration can be continued until about three weeks after last dose of the agents of the combination therapy. Typical amount of Cyanocobolamin is 1000 mcg (4). One preferred aspect of the invention is a method for treatment of melanoma in a patient in need thereof comprising the steps of (a) administering to said patient ONCOS-102 adenovirus and a checkpoint inhibitor and a step of administration of Cyanocobolamin to the patient.

Folic acid and Cyanocobolamin are generally used to reduce treatment related hematologic and gastrointestinal toxicity.

Also Dexamethasone can be administered to a patient subject to the combination therapy. Typically, Dexamethasone is administered day before, the day of and the day after administering of the other agents of the combination therapy. Dexamethasone can be administered 4 mg BD (i.e. twice a day) for 5 days, and in a three-weekly frequency for up to six cycles. One object of the invention is a method for treatment of melanoma in a patient in need thereof comprising the steps of (a) administering to said patient ONCOS-102 adenovirus and a checkpoint inhibitor, and (b) administrating Dexamethasone to the patient.

The combination therapy as described herein can further comprise administration of cyclophosphamide to the patient. One object of the invention is a method for treatment of melanoma in a patient in need thereof comprising a step (a) of administering to said patient ONCOS-102 adenovirus and two chemotherapeutic agents and further comprising before step (a) administration of Cyclophosphamide to the patient.

One further aspect of the invention is a method for reducing tumor growth in a patient, wherein said method comprises administering ONCOS-102 adenovirus and a checkpoint inhibitor or checkpoint inhibitors to said patient under conditions wherein tumor growth in said patient is reduced.

The method can comprise identifying the patient as having a tumor before administering the combination therapy. The tumor diagnosis can be done in any conventional method. The patient can be identified as having the tumor using for example a diagnostic imaging technique. The method can further comprise measuring a tumor growth reduction after administering the combination therapy to the patient. The tumor reduction can be studied by any conventional method. The tumor growth reduction can be measured for example using a diagnostic imaging technique.

Another aspect of the present invention is the use of combination therapy in order to inhibit the growth of tumor. Marks of the inhibition of the tumor growth may for example be a reduction in tumor weight and reduction in tumor volume. In addition, the combination therapy can be used to inhibit the spread of tumor.

It should be also noted that tumor pseudoprogression that corresponds to an increase of lesion size related to treatment, may affect the result of imaging follow-up intended to reveal the effect of the current combination therapy on the tumor size. This kind of effect has been observed after combined chemotherapy and radiotherapy in about 30% of patients. Pseudoprogression may thus be present in certain part of the patients when the combination therapy as described herein is used. For those patients reduction of tumor size is not a suitable indicator of the effectiveness of the therapy.

Also disclosed is a method of reducing the growth of cancer cells comprising administering to a subject in need of treatment an effective amount of ONCOS-102 adenovirus and a checkpoint inhibitor or checkpoint inhibitors.

A method of inhibiting or killing tumor or cancer cells in a human patient, consisting of treating the patient with ONCOS-102 adenovirus and a checkpoint inhibitor or checkpoint inhibitors, wherein the checkpoint inhibitor is a PD-1 or PD-L1 inhibitor, or any combination thereof, is also disclosed.

Further, a method of killing tumor or cancer cells comprising contacting the tumor or cancer cells with ONCOS-102 adenovirus the checkpoint inhibitor or checkpoint inhibitors, wherein the checkpoint inhibitor is a PD-1 or PD-L1 inhibitor, or any combination thereof, is disclosed.

Further, also disclosed is a method for treating human cancer, such as advanced melanoma, comprising administering to a subject in need thereof an effective amount of ONCOS-102 adenovirus and effective amounts of a checkpoint inhibitor or checkpoint inhibitors to provide a combination therapy having an enhanced therapeutic effect compared to the effect of the ONCOS-102 adenovirus administered alone or of the checkpoint inhibitor or checkpoint inhibitors administered without said virus.

In an embodiment of the invention, ONCOS-102 acts as an in situ cancer vaccine. As used herein "in situ cancer vaccine" refers to a cancer vaccine, which both kills tumor cells and also increases the immune response against tumor cells. Virus replication is a strong danger signal to the immune system (=needed for a TH1 type response), and thus acts as a powerful costimulatory phenomenon to GM-CSF mediated maturation and activation of APCs, and recruitment of NK cells. Tumor cell lysis also helps to present tumor fragments and epitopes to APCs and furthermore, costimulation is produced by inflammation. Thus, an epitope independent (i.e. not HLA restricted) response is produced in the context of each tumor and therefore takes place in situ. Tumor specific immune response is activated in the tumor environment when specific tumor antigens are released from dying cells upon tumor cell lysis.

In a preferred embodiment of the invention, the method or use further comprises administration of concurrent radiotherapy to a subject.

In a preferred embodiment of the invention, the method or use further comprises administration of autophagy inducing agents to a subject. Autophagy refers to a catabolic process involving the degradation of a cell's own components through the lysosomal machinery. "Autophagy inducing agents" refer to agents capable of inducing autophagy and may be selected from a group consisting of, but not limited to, mTOR inhibitors, PI3K inhibitors, lithium, tamoxifen, chloroquine, bafilomycin, temsirolimus, sirolimus and temozolomide. In a specific embodiment of the invention, the method further comprises administration of temozolomide to a subject. Temozolomide may be either oral or intravenous temozolomide.

An object of the invention is thus ONCOS-102 adenovirus for use in the treatment of human cancer, wherein the virus is administered in combination with a checkpoint inhibitor or checkpoint inhibitors to a patient.

In the combination therapy as described herein, ONCOS-102 adenovirus and checkpoint inhibitor or checkpoint inhibitors can be administered in several doses and at different times.

Another object of the invention is ONCOS-102 adenovirus for use in the treatment of human cancer, wherein the human cancer is selected from the group consisting of advanced melanoma, renal cancer, ovarian cancer, bladder cancer, prostate cancer, breast cancer, colorectal cancer, lung cancer, gastric cancer, classical Hodgkin lymphoma, mesothelioma, and liver cancer.

Still another object of the invention is ONCOS-102 adenovirus for use in the treatment of human cancer, wherein the human cancer is advanced melanoma.

A further object of the invention is ONCOS-102 adenovirus for use in the treatment of human cancer, wherein the checkpoint inhibitor is an anti-PD-1 antibody or an anti-PD-L1 antibody, or any combination thereof.

A further object of the invention is ONCOS-102 adenovirus for use in the treatment of human cancer, wherein the anti-PD-1 antibody is pembrolizumab or nivolumab.

Still another object of the invention is ONCOS-102 adenovirus for use in the treatment of human cancer, wherein the anti-PD-L1 antibody is durvalumab.

A further object of the invention is ONCOS-102 adenovirus for use in the treatment of human cancer, wherein the amount of the virus is from $5\times10^{10}$ to $5\times10^{11}$ VP.

ONCOS-102 adenovirus for use in the treatment of human cancer, wherein the virus is administered in an amount of $3\times10^{11}$ VP, is also an aspect of the invention.

According to one aspect of the invention, ONCOS-102 adenovirus for use in the treatment of human cancer, wherein the virus is administered by direct injection into tumor and the checkpoint inhibitor or checkpoint inhibitors is/are administered intravenously.

ONCOS-102 adenovirus for use in the treatment of human cancer, wherein the virus is administered before administering of the checkpoint inhibitor or checkpoint inhibitors and optionally the virus is administered also during administering period of said checkpoint inhibitor or checkpoint inhibitors and/or after administering the checkpoint inhibitor or checkpoint inhibitors, is also an aspect of the invention.

One object of the invention is a method for treating cancer in a patient comprising a step of administering to said patient ONCOS-102 adenovirus and a checkpoint inhibitor or checkpoint inhibitors.

A preferred embodiment is a method for treating cancer in a patient comprising a step of administering to said patient ONCOS-102 adenovirus and a checkpoint inhibitor or checkpoint inhibitors, wherein said cancer is advanced melanoma.

According to one preferred embodiment, in a method for treating cancer in a patient comprising a step of administering to said patient ONCOS-102 adenovirus and a checkpoint inhibitor or checkpoint inhibitors, the checkpoint inhibitor or checkpoint inhibitors is/are anti-PD-1 antibody or anti-PD-L1 antibody, or any combination thereof.

According to another preferred embodiment, the anti-PD-1 antibody pembrolizumab or nivolumab is used in the method for treating cancer in a patient said method comprising a step of administering to said patient ONCOS-102 adenovirus and a checkpoint inhibitor or checkpoint inhibitors. Preferably the anti-PD-L1 antibody is durvalumab. Thus, the anti-PD-1 antibody is preferably pembrolizumab or nivolumab and the anti-PD-L1 antibody is preferably durvalumab.

One preferred embodiment is a method for treating cancer in a patient comprising a step of administering to said patient ONCOS-102 adenovirus and a checkpoint inhibitor or checkpoint inhibitors, wherein the virus is administered before administering of the checkpoint inhibitor or checkpoint inhibitors and optionally the virus is administered also during administering period of said checkpoint inhibitor or checkpoint inhibitors and/or after administering the checkpoint inhibitor or checkpoint inhibitors.

Another preferred embodiment is a method for treating cancer in a patient comprising a step of administering to said patient ONCOS-102 adenovirus and a checkpoint inhibitor or checkpoint inhibitors, wherein ONCOS-102 adenovirus is administered from one to ten times and the checkpoint inhibitor is administered from 1 to 15 times to said patient.

Still another preferred embodiment is a method for treating cancer in a patient comprising a step of administering to said patient ONCOS-102 adenovirus and a checkpoint inhibitor or checkpoint inhibitors, wherein the amount of ONCOS-102 adenovirus to be administered is in the range of $5\times10^{10}$-$5\times10^{11}$ VP.

Another aspect of the invention is a method for treating cancer in a patient comprising a step of administering to said patient ONCOS-102 adenovirus and a checkpoint inhibitor or checkpoint inhibitors further comprising administration of Cyclophosphamide before step of administering ONCOS-102 adenovirus and checkpoint inhibitor or checkpoint inhibitors to the patient in need thereof.

Use of ONCOS-102 adenovirus in the treatment of human cancer, wherein the virus is administered to a patient in need thereof in combination with a checkpoint inhibitor or checkpoint inhibitors, is also an aspect of the invention.

An object of the present invention was to develop novel therapeutically effective use of ONCOS-102 oncolytic adenovirus and a checkpoint inhibitor or checkpoint inhibitors with improved safety properties and with improved effect on cancer as compared to using viral therapy alone or checkpoint inhibitor or checkpoint inhibitors only.

Besides enabling the transport of the vector to the site of interest the adenovirus vector of the invention also assures the expression and persistence of the transgene. Furthermore, immune response against the vector as well as the transgene is minimized.

The present invention solves problems related to therapeutic resistance to conventional treatments. Furthermore, the present invention provides tools and methods for selective treatments, with less toxicity or damages in healthy tissues. Advantages of the present invention include also different and reduced side effects in comparison to other therapeutics. Importantly, the approach is synergistic with many other forms of therapy including radiation therapy, and is therefore suitable for use in combination regimens.

The present invention achieves cancer therapy, wherein tumor cells are destroyed by virion-caused oncolysis. In addition, various different mechanisms activating human immune response, including activation of natural killer cells (NK) and dendritic cells (DC) are recruited for therapeutic use in the present invention.

This application thus describes strategies and provides methods and means to both effectively recruit the host's immune system against malignant cells and simultaneously provide direct oncolytic and checkpoint protein inhibiting effect in malignant cells, while maintaining an excellent safety record.

Aspects of the invention are directed to novel methods and means for achieving efficient and accurate gene transfer as well as increased specificity and sufficient tumor killing ability in cancer therapy.

In summary, presented data give a strong rationale for combining ONCOS-102 with a checkpoint inhibitor or checkpoint inhibitors for the treatment of human cancer.

EXAMPLES

The following examples are given solely for the purpose of illustrating various embodiments of the invention and they are not meant to limit the present invention. One skilled in the art will appreciate readily that the present invention is well adapted to carry out the objects and obtain the aims and advantages mentioned above, as well as those objects, aims and advantages inherent herein. Changes therein and other uses which are encompassed within the spirit of the invention as defined by the scope of the claims will occur to those skilled in the art.

Construction of ONCOS-102

The construction and characterization of chimeric oncolytic adenovirus coding for human GM-CSF (ONCOS-102) has been described previously (WO 2010/072900 and Koski et al.) Shortly, Ad5/3-D24-GMCSF was generated and amplified using standard adenovirus preparation techniques. A pAdEasy-1-derived plasmid containing a chimeric 5/3 fiber, pAdEasy5/3, was created by homologous recombination in *Escherichia coli* of Ad5/3luc1 viral genome and BstXI-digested 8.9 kb fragment of pAdEasy-1. Next, a shuttle vector containing a 24-bp deletion in E1A (pShuttleD24) was linearized with PmeI and recombined with pAdEasy5/3 resulting in pAd5/3-D24. In order to insert human GMCSF gene into E3 region, an E3-cloning vector pTHSN was created by inserting SpeI to NdeI fragment from Ad5 genome into the multicloning site of pGEM5Zf+ (Promega, Madison, Wis.). pTHSN was further digested with SunI/MunI creating a 965-bp deletion in E3 region (6.7K and gp19K deleted). The 432 bp complementary DNA encoding human GM-CSF (Invitrogen, Carlsbad, Calif.) was amplified with primers featuring specific restriction sites SunI/MunI flanking the gene and then inserted into SunI/MunI-digested pTHSN. pAd5/3-D24-GMCSF was generated by homologous recombination in *E. coli* between FspI-linearized pTHSN-GMCSF and SrfI-linearized pAd5/3-D24. Ad5/3-D24-GMCSF virus genome was released by Pad digestion and transfection to A549 cells for amplification and rescue. All phases of the cloning were confirmed with PCR and multiple restriction digestions. The shuttle plasmid pTHSN-GM-CSF was sequenced. Absence of wild-type E1 was confirmed with PCR. The E1 region, transgene, and fiber were checked in the final virus with sequencing and PCR. Virus production was done, according to the principles of cGMP by Oncos Therapeutics (Helsinki, Finland), on A549 cells to avoid the risk of wild-type recombination. Virus stock buffer formulation was 10 mmol/l Trizma base, 75 mmol/l NaCl, 5% (wt/vol) sucrose, 1 mmol/l MgCl, 10 mmol/l L(+)histidine, 0.5% (vol/vol) EtOH, 0.02% Tween, 100 µmol/l EDTA; 0.9% (wt/vol) NaCl solution (B. Braun, Melsungen, Germany) was used as a diluent. ONCOS-102 was produced by Biovian (Turku, Finland) in GLP and stored at −80° C. until use. For use, ONCOS-102 was thawed shortly before application and stored on ice until use. After thawing, ONCOS-102 was diluted in laminar flow box to obtain the required concentration, injection syringes were prepared and stored on ice until use.

Cell Lines

A-375 human melanoma cells (ATCC CRL-1619™), $2\times10^6$ cells/flank, were cultured at 37° C. with 5% $CO_2$ in DMEM with 4500 mg/ml glucose (Sigma-55671) supplemented with 10% heat-inactivated FBS (South Africa origin, Dutscher P30-1506) and 1% Penicillin/Streptomycin (Dutscher L0018). The same culturing protocol applies also to SK-MEL2 (ATCC HTB-68) human melanoma cells.

Checkpoint Inhibitors (CPI):

For pembrolizumab (Keytruda) the human dose is 2 mg/kg, and after extrapolation 40 µg/mouse was used. For nivolumab (Opdivo) the human dose is 3 mg/kg, and after extrapolation 60 µg/mouse was used. Extrapolated dose of CPI, bearing in mind that mouse weight is 20 g. For Durvalumab the human dose can be 10-20 mg/kg (currently, the recommended dosing schedule for Durvalumab is 20 mg/kg Q4W or 10 mg/kg Q2W. This is being transitioned to a fixed dosing for Durvalumab, based on information from MedImmune, which indicates that the dose and schedule of 1500 mg Durvalumab Q4W was selected based on PK models), after extrapolation 200 µg-400 µg/mouse can be used Extrapolated dose of CPI, bearing in mind that mouse weight is 20 g.

Animal Selection, Randomization, Group Assignment, Housing, Diet and Water and Acclimation Animals were sorted randomly in to the groups. Animal groups were kept in separate cages with study cards attached to the cages. The cards were marked with the study number, treatment group, individual animal IDs, as well as their origin and date of arrival. The individual animals in each cage were marked with ear piercing for identification. Only one cage was handled at a time to avoid mixing the animals between the cages.

The animals were housed in biosafety level 2 (BSL2) facility in humidity- and temperature monitored environment. Animals were housed in individually ventilated plastic cages with a filter lid (GreenLine, Scanbur).

The animals fed standard pelletized diet provided ad libitum. Water was supplied ad libitum during the acclimation and study periods.

Animals were acclimated for 7 days prior to starting the experimental part. All the animals remained in good health throughout the acclimation period.

Analysis of Tumor Size Progression

Tumor sizes were measured and recorded starting 7-11 days after the cell injections. The first day of treatment and first day of tumor size measurement are indicated as day 0. Tumors were measured every three days.

The longest and shortest diameter were recorded and the tumor volume was calculated using a formula of (width×length×height)/2.

Body weight was measured every 3 days throughout the whole experiment.

Tumor volumes: An absolute tumor volume was the end point in tumor volume analysis. Analysis of variance for repeated measurements was applied as analysis method for tumor volumes as there were two tumors measured for each mouse. The model contained the group effect and the baseline value as covariate as fixed effects. Pair-wise comparisons between groups were adjusted with Tukey's method. Synergism calculation was done by using FTV (fractional tumor volume) method.

Human Melanoma Xenograft Model

The experiments have been carried out by TCS at Archamps, France with NOD/Shiscid/IL-2Rγnull immunodeficient mouse strain (NOG). Four week-old immunodeficient NOG mice (Taconic) were engrafted with cord blood-derived CD34+ hematopoietic stem and progenitor cells (French blood institute) two days after chemical myeloablative treatment. Engraftment consisted in intravenous injection CD34+ cells. Fourteen weeks after cell injection, engraftment level was monitored with the analysis of human CD45+ cells among total blood leukocytes by flow cytometry (Attune, Life technologies). For this pilot study, only mice with a humanized rate (defined as the ratio of circulating hCD45+/total leukocytes) higher than 20% were selected. We used only female mice. All animal studies described in this study have been reviewed and approved by the local ethic committee (01_TransCurebioServices-AB-01). Mice have been hosted by groups of 3-5 individuals. Each mouse has been uniquely identified. Animals have been housed in a ventilated cage (type II (16×19×35 cm, floor area=500 cm2)) under the following controlled conditions:

Room temperature (22±2° C.)
Hygrometry (55±10%)
Photoperiod (12:12-hour light-dark cycle 7 am to 7 pm)
Water and food (Ref. 2018, Harlan France) available ad libitum Mice were anesthetized with isoflurane Forane (Baxter), A-375 cells in×100 µl were injected into both flanks (2E+06/flank). One or two tumors were induced in each mouse. Tumors were let to grow 7-11 days prior to the treatments. Viruses were administered days 1, 3 and 5 after tumor formation and checkpoint inhibitors (Keytruda and Opdivo) were administered on days 9, 13 and 17 after tumor formation, respectively. When systemic effect was studied, only one tumor/mouse was treated (see FIG. 1C). Mock animals were treated with 0.9% saline. ONCOS-102 was diluted into 0.9% saline and injected intratumorally at a dose of $5\times10^7$ VP per tumor. Injections were given in a fan-like pattern to ensure even distribution throughout the tumor. Checkpoint inhibitors (Keytruda and Opdivo) were diluted in 0.9% NaCl and administrated intraperitoneally at doses of 40 µg/mouse (weight 20 g) of Keytruda and 60 µg/mouse of Opdivo, respectively. The injection volume was 50 µl of checkpoint inhibitor.

The longest and shortest diameter were recorded and the tumor volume was calculated using a formula of (width× length×height)/2.

Example 1

Improved Antineoplastic Activity Against Melanoma in Mice by Using ONCOS-102 Combined with a Checkpoint Inhibitor In the present study the mice were either not treated or treated with ONCOS-102 only, with a checkpoint inhibitor only or with a combination of ONCOS-102 and a checkpoint inhibitor. The study groups 1-9, number of mice and minimum turn-around times used are shown in Table 1. Shortly, in the study group 1, immunodeficient mice were treated with $5\times10^6$ VP of ONCOS-102. In group 2, $5\times10^7$ VP of ONCOS-102 was used instead, whereas mice in group 3 received no treatment at all. The results obtained by measuring tumor volume from these groups are shown in FIG. 1 A. The results demonstrate that the tumor volume diminished virus-dose dependently.

Humanized mice in group 4 were treated with $5\times10^7$ VP of ONCOS-102, while mice at group 5 were left untreated. Humanized mice of groups 6 and 7 were treated with Keytruda (40 µg/mouse) and Opdivo (60 µg/mouse), respectively. Humanized mice in group 8 were first treated with ONCOS-102 ($5\times10^7$ VP), followed by Keytruda (40 µg/mouse). In group 9, the mice had two tumors (left and right, respectively). The mice were treated otherwise as in group 8, but only the right tumor was treated with the virus. The results of the treated right tumor as compared to untreated left tumor of humanized mice in group 9 and tumors of humanized mice with treatment with Keytruda only (group 6) are shown in FIG. 1 C and demonstrate a systemic effect of the virus treatment, as both the virus-treated tumor and virus untreated tumor are similarly affected. In FIG. 1 B a comparison between untreated immunodeficient and humanized mice of groups 3 and 5 is shown. The results demonstrate that human immune system inhibits the tumor growth in mice. In FIG. 1 D, the differences between mice of groups 8 (ONCOS-102+ Keytruda) and 4 (ONCOS-102 only) and groups 8 and 6 (Keytruda only) suggest that the combination therapy, wherein the tumor is first primed with ONCOS-102 before administering the checkpoint inhibitor, is more efficient than treating with ONCOS-102 alone or with Keytruda without priming.

TABLE 1

Study groups of the experiment (groups 1-9).

| Group number | Treatment | Number of mice |
|---|---|---|
| 1 NOG | Oncolytic virus (5 × 10^6 VP/tumor) | 2 |
| 2 NOG | Oncolytic virus (5 × 10^7 VP/tumor) | 2 |
| 3 NOG | No treatment | 2 |
| 4 huNOG | Oncolytic virus (5 × 10^7 VP/tumor) | 2 |
| 5 huNOG | No treatment | 2 |
| 6 huNOG | Keytruda | 2 |
| 7 huNOG | Optivo | 2 |
| 8 huNOG | Oncolytic virus (5 × 10^7 VP/mouse) + Keytruda | 2 |
| 9 huNOG | Oncolytic virus (5 × 10^7 VP/mouse) + Keytruda, only right tumor treated | 2 |

Example 2

Evaluation of the Efficacy of the Combination Therapy

The experiments were carried out by TCS at Archamps, France with NOD/Shi-scid/IL-2Rγnull immunodeficient mouse strain (NOG). Four-week-old immunodeficient NOG mice (Taconic) were engrafted with cord blood-derived CD34+ hematopoietic stem and progenitor cells (French Blood Bank) two days after chemical myeloablative treatment. Engraftment consisted in intravenous injection of CD34+ cells. Fourteen weeks after cell injection, engraftment level was monitored with the analysis of human CD45+ cells among total blood leukocytes by flow cytometry (Attune, Life technologies). Humanization rate was defined as the ratio of circulating hCD45+/total CD45+ (mCD45+hCD45). Sixty humanized NOG mice were engrafted with A2058 tumor cells and randomized into 8 groups.

8 groups of 6 to 8 mice were randomized and treated as followed:

Group 1: N=8. Vehicle. Vehicle (PBS): Day 15, 16 and 18 (intra-tumor on both tumors) and intravenously Day 15, 16 and 18 and every 3-4 days throughout the study.

Group 2: N=8. ONCOS-102. ONCOS-102 (2.5×106 VP/tumor=>5×106 VP/mouse): Day 15, 16 and 18 (intra-tumor, both tumors).

Group 3: N=8. Keytruda 200: Keytruda 200 µg/mouse: intravenously Day 15, 16 and 18 and every 3-4 days throughout the study.

Group 4: N=8. Keytruda 400: Keytruda 400 µg/mouse: intravenously Day 15, 16 and 18 and every 3-4 days throughout the study.

Group 5: N=8. ONCOS-102+ Keytruda 200: Oncolytic virus (2.5×106 VP/tumor=>5×106 VP/mouse) and Keytruda 200 µg/mouse: Day 15, 16 and 18 (intra-tumor, both tumors) and intravenously Day 15, 16 and 18 and every 3-4 days throughout the study.

Group 6: N=8. ONCOS-102+ Keytruda 400. Oncolytic virus (2.5×106 VP/tumor=>5×106 VP/mouse) and Keytruda 400 µg/mouse: Day 15, 16 and 18 (intra-tumor, both tumors) and intravenously Day 15, 16 and 18 and every 3-4 days throughout the study.

Group 7: N=6. OV Right+Keytruda 200: Oncolytic virus (5×106 VP/tumor) and Keytruda 200 µg/mouse: Day 15, 16 and 18 (intra-tumor on right tumor) and intravenously Day 15, 16 and 18 and every 3-4 days throughout the study.

Group 8: N=6. OV Right+Keytruda 400: Oncolytic virus (5×106 VP/tumor) and Keytruda 400 µg/mouse: Day 15, 16 and 18 (intra-tumor on right tumor) and intravenously Day 15, 16 and 18 and every 3-4 days throughout the study.

Tumor volumes were monitored 3 times per week using calipers. When large enough to be measured, tumor volumes were calculated using the formula: (Length×(Width) 2/2). A tumor volume exceeding 1000 mm3 was considered as an end point and in this case, mice were sacrificed. Sacrifice was scheduled on Day 40.

All parameters were analyzed using GraphPad Prism software (version 7). Statistical analyses were performed as followed. One-way ANOVA with Tukey's post test was applied to compare the groups. At day 40, t-test was applied to compared each treated group to the vehicle group. For survival analysis, a Kaplan-Meier curve was plotted and a log rank (Mantel-Cox) test used.

Figure 2:
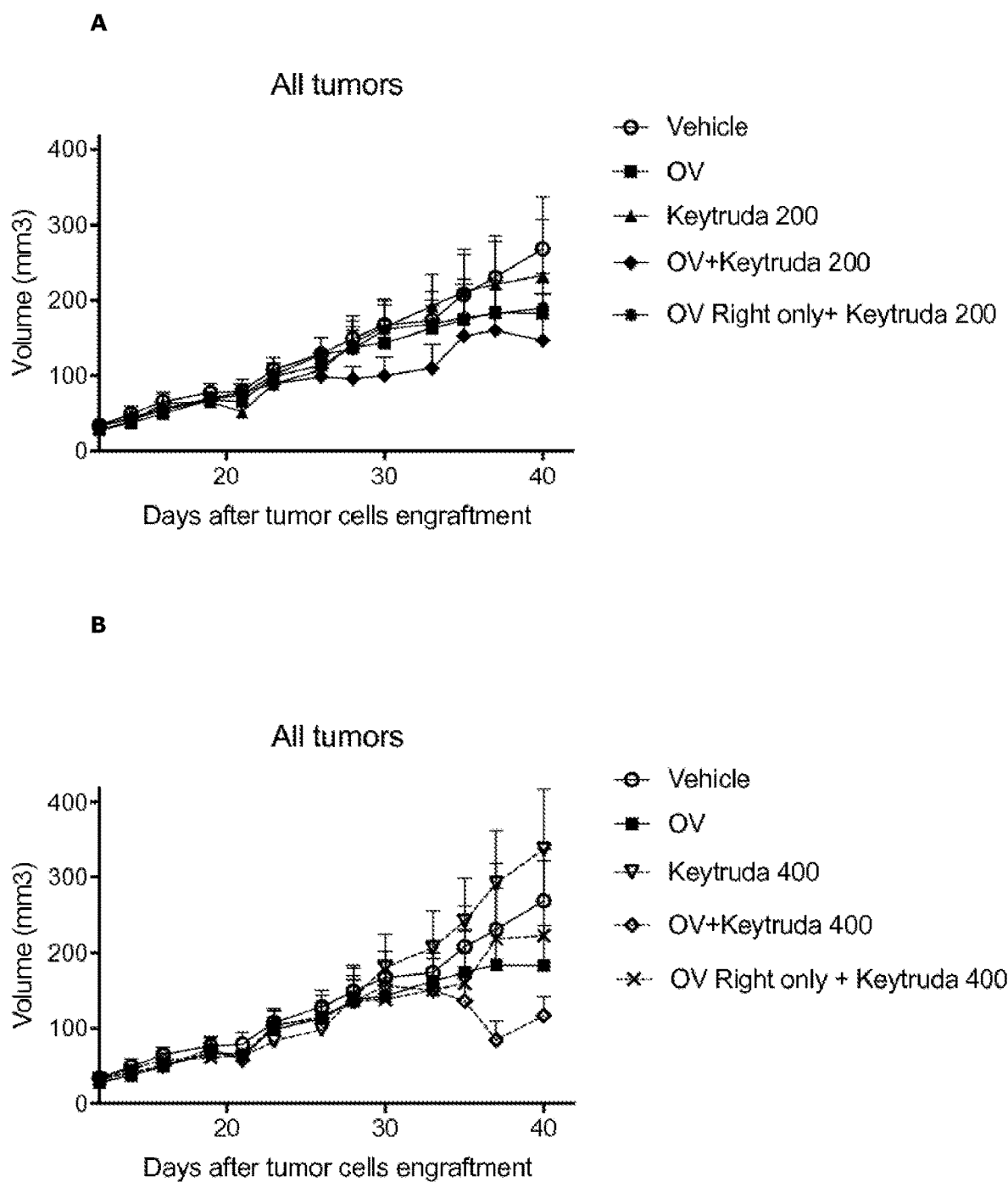
FIG. 2. Tumor growth analyses. N=6-8 (12-16 tumours pen animal). Results are presented as mean+/−SD, *<0.05.

We observed (FIG. 2) that ONCOS-102 reduced tumor volume compared to vehicle treated group. Keytruda alone has no significant effect but combination of ONCOS-102 with Keytruda 200 µg/mouse and Keytruda 400 µg/mouse significantly reduced tumor volume (p=0.0034 and p=0.0023 respectively) compared to vehicle group. The combination of ONCOS-102 and Keytruda 200 and 400 µg/mouse reduced tumor volume by 46 and 57% respectively.

Immune cell infiltration of tumor was analyzed by flow cytometry at sacrifice. Analysis was performed on tumors collected on Day 40, at the end of the study.

Figure 3:
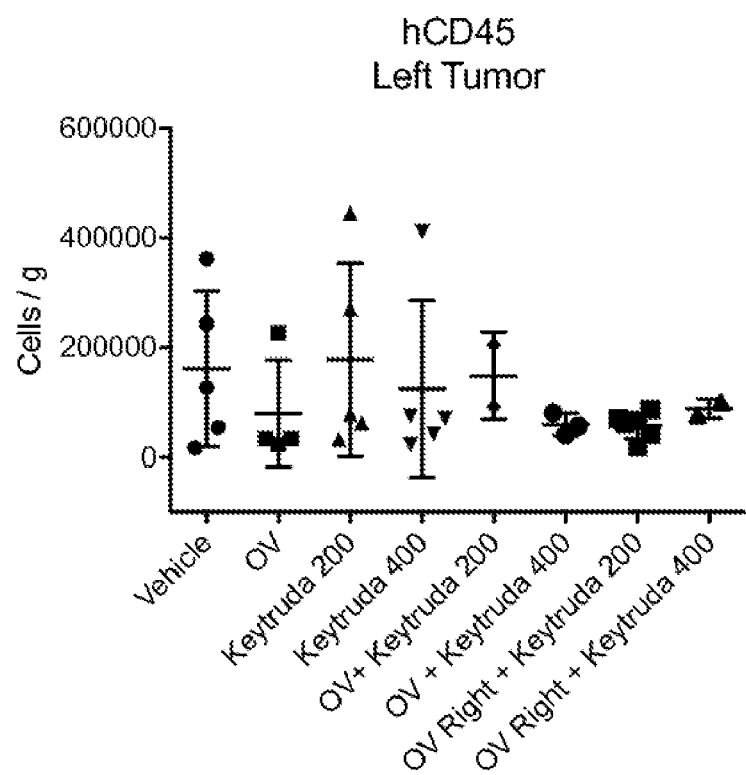
FIG. 3. Immune cell infiltration. Number of human CD45 leukocytes was quantified and expressed as number of cells per gram of tumor on the left flank (left panel) and the right flank (right panel). Results are presented as mean+/−SD. N=2-6. *<0.05 vs OV+Keytruda 200.
Figure 3:
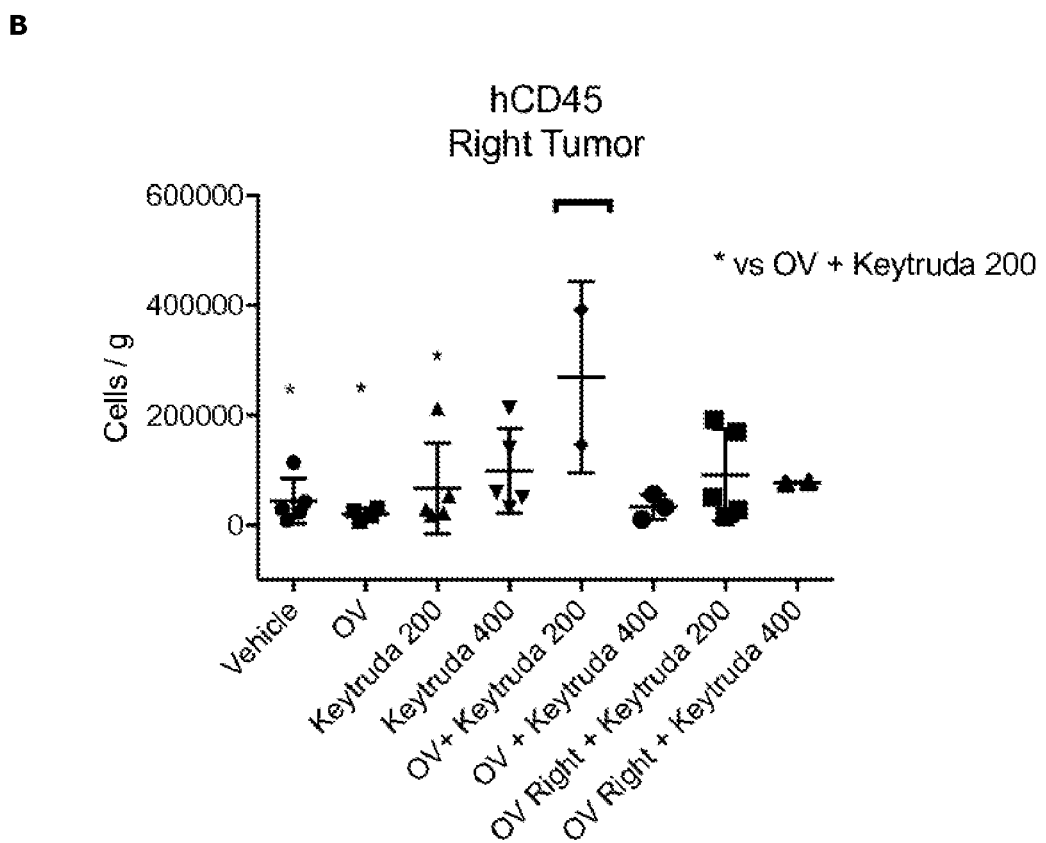

The amount of total human CD45+ was first investigated (FIG. 3). In the left tumor, no difference between the groups was observed. In the right tumor (treated locally), the number of immune CD45 cells was increased in the ONCOS-102+Keytruda 200 group by comparison to the vehicle, the ONCOS-102 and the Keytruda 200 group which might indicate a synergistic effect of ONCOS-102 and Keytruda 200 to increase the recruitment of human immune cells.

Figure 4:
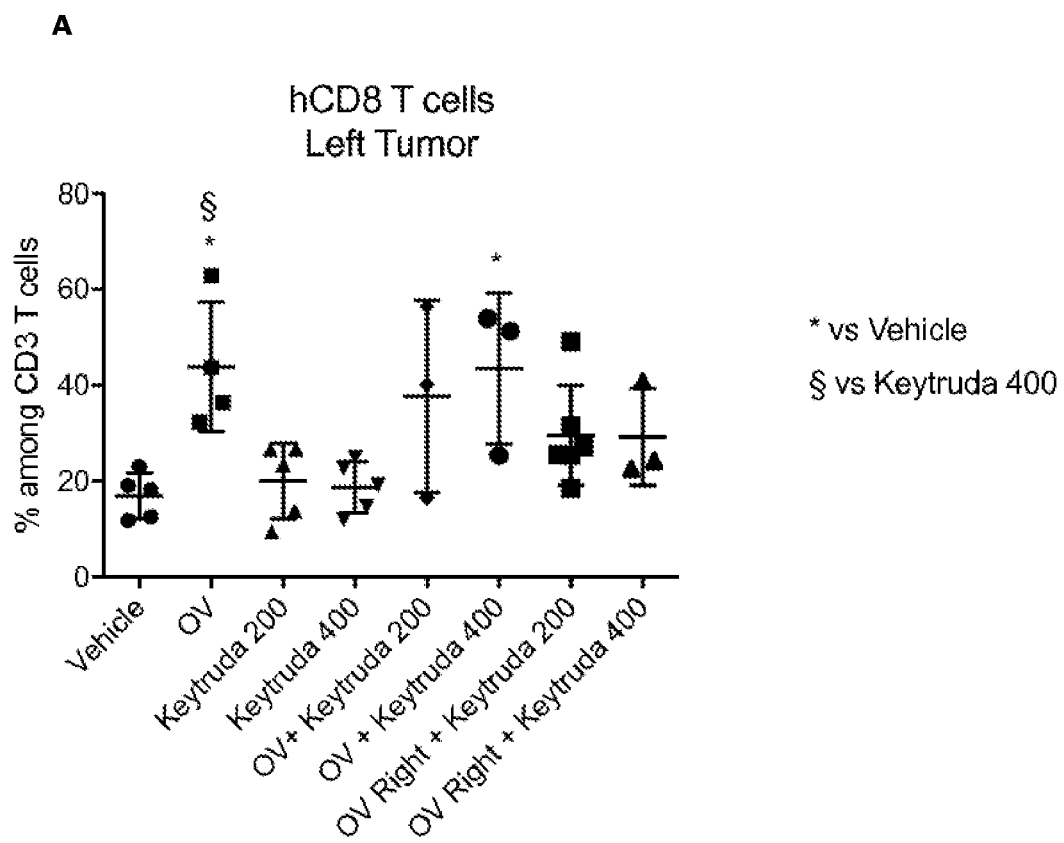
FIG. 4. Immune cell infiltration. % of human CD8+ T cells among CD3+ leukocytes was quantified on the left flank (left panel) and the right flank (right panel). Results are presented as mean+/−SD. n=2-6. *<0.05 **<0.01 vs vehicle. §<0.05, §§<0.01 vs Keytruda 400. #<0.05 vs Keytruda 200.
Figure 4:
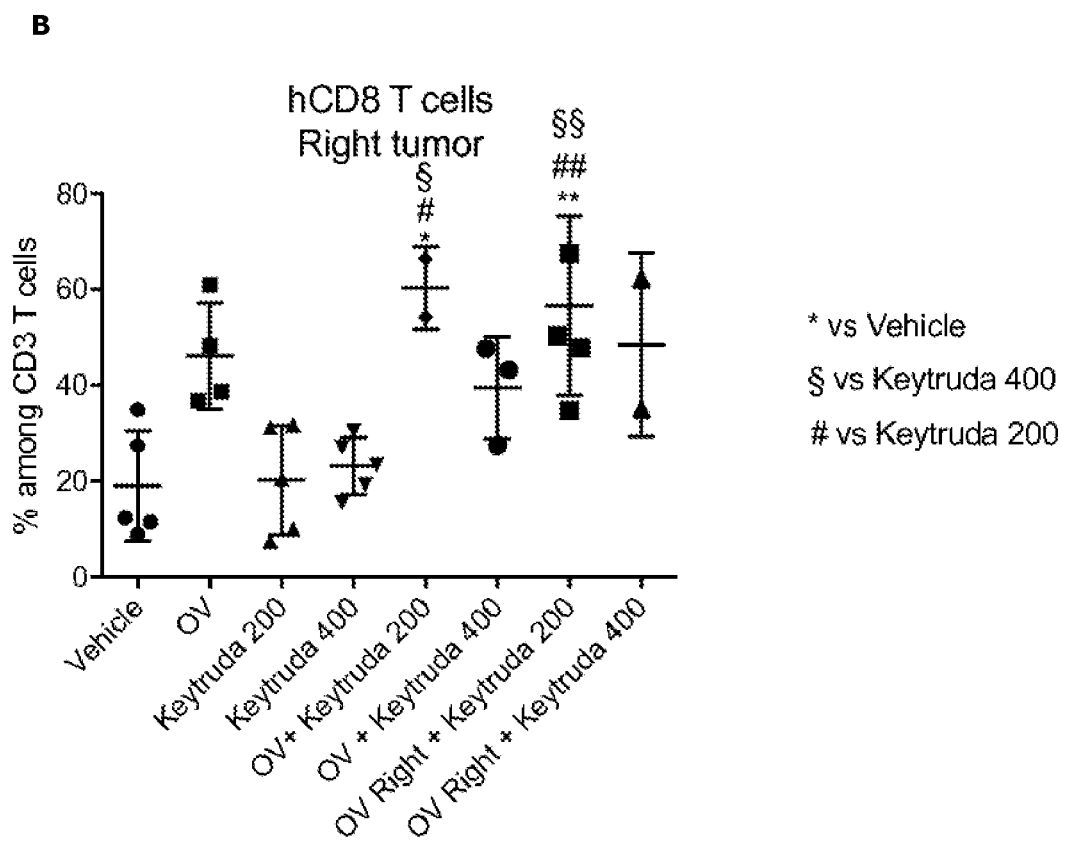

On the left flank and on the right flank, a significant increase of CD8+ T cells was observed in the OV treated group and the groups treated with ONCOS-102+ Keytruda. On the right flank, we also observed a significant increase of the proportion of CD8+ T cells in the right tumors but not in the left tumors by comparison to the vehicle group. Keytruda 200 and Keytruda 400 did not have an effect on the proportion of CD8+ T cells (FIG. 4).

Figure 5:
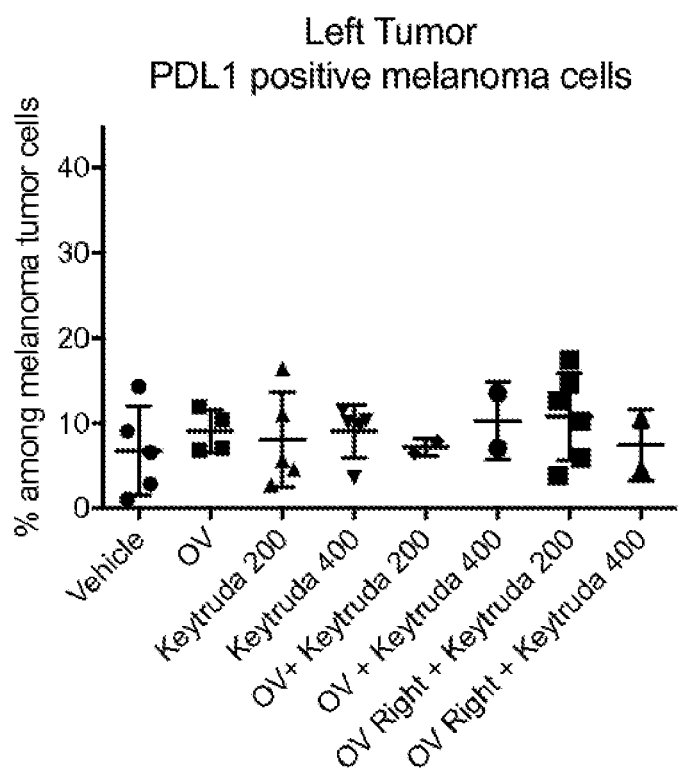
FIG. 5. PDL1 expression at the surface of melanoma cells on the tumors. Results are expressed as % of PDL1 positive cells among melanoma cells. Results show mean+/−SD.
Figure 5:
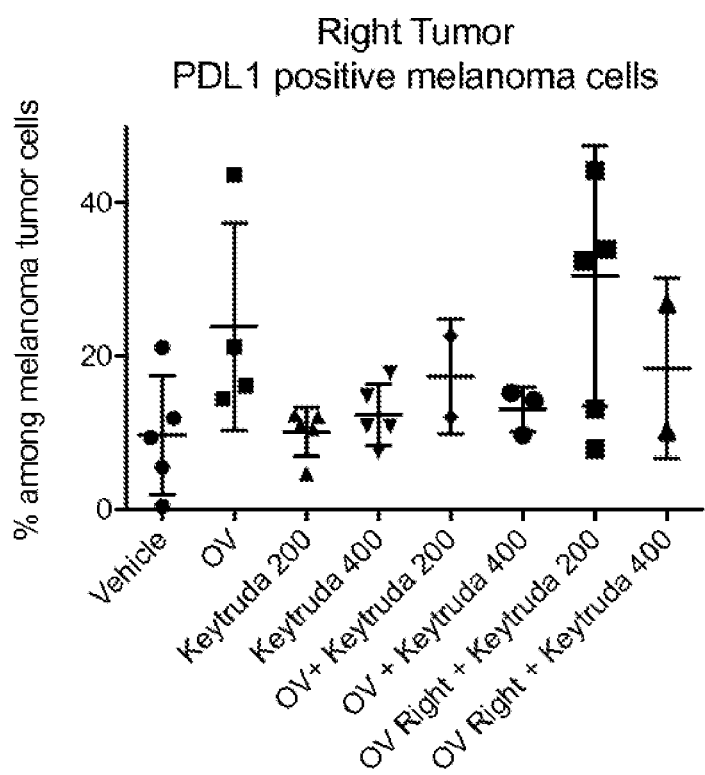

PDL1 expression was also investigated at the surface of melanoma cells (FIG. 5). PDL1 was expressed at the surface of melanoma cells in the tumors and no significant difference of expression was observed between the groups.

In addition, it was shown that the combination of ONCOS-102 and Keytruda 200 and 400 µg/mouse shown synergistic anti-tumor effect (Table 2).

TABLE 2

Combined treatment of melanoma with ONCOS-102 and Keytruda 200 µg or Keytruda 400 µg in huNOG mice. Assessment of therapeutic synergy with FTV calculation method. FTV (mean tumor volume (%) experimental)/(mean tumor volume control (%)).

| | | | | in vivo | | | | | |
| --- | --- | --- | --- | --- | --- | --- | --- | --- | --- |
| | | | | OV + Keytruda 200 µg | | | OV + Keytruda 400 µg | | |
| Day | OV | Keytruda 200 | Keytruda 400 | Exp.* | Obs.** | Ratio | Exp.* | Obs.** | Ratio |
| 26 | 0.88 | 0.95 | 0.87 | 0.83 | 0.76 | 1.1 | 0.77 | 0.88 | 0.88 |
| 37 | 0.68 | 0.91 | 1.26 | 0.62 | 0.42 | 1.47 | 0.86 | 0.40 | 2.14 |

*(Mean FTV of Keytruda (%)) × (mean FTV of ONCOS-102 (%)).
**(expected FTV divided by the observed FTV).
A ratio (R) of >1 indicates a synergistic effect, and a ratio of <1 indicates a less than additive effect.

REFERENCES

Fueyo J., Gomez-Manzano C., Alemany R., Lee P., McDonnell T J., Mitlianga P. Shi Y-X., Levin V A., Yung W K A. and Kyritsis A P. A mutant oncolytic adenovirus targeting the Rb pathway produces anti-glioma effect in vivo. *Oncogene* (2000) 19:2-12.

Heise C., Hermiston T., Johnson L., Brooks G., Sampson-Johannes A., Williams A., Hawkins L. & Kirn D. An adenovirus E1A mutant that demonstrates potent and selective systemic anti-tumoral efficacy. *Nat Med* (2000) 6:1134-9.

Hanahan D, Weinberg R A. (2000). The hallmarks of cancer. *Cell* (2000) 100: 57-70.

Koski A, Kangasniemi L, Escutenaire S, Pesonen S, Cerullo V, Diaconu I, Nokisalmi P, Raki M, Rajecki M, Guse K, Ranki T, Oksanen M, et al. Treatment of cancer patients with a serotype 5/3 chimeric oncolytic adenovirus expressing GMCSF. *Mol Ther* (2010) 18: 1874-84.

Ranki T, Joensuu T, Jäger E, Karbach J, Wahle C, Kairemo K, Alanko T, Partanen K, Turkki R, Linder N, Lundin J, Ristimäki A, et al. Local treatment of a pleural mesothelioma tumor with ONCOS-102 induces a systemic antitumor CD8+T-cell response, prominent infiltration of CD8+ lymphocytes and Th1 type polarization. *OncoImmunology* (2014) 3: e958937.

Ranki T, Pesonen S, Hemminki A, Partanen K, Kairemo K, Alanko T, Lundin J, Linder N, Turkki R, Ristimäki A, Jager E, Karbach J, Wahle C, Kankainen M, Backman C, von Euler M, Haavisto E, Hakonen T, Heiskanen R, Jaderberg M, Juhila J, Priha P, Suoranta L, Vassilev L, Vuolanto A, Joensuu T. Phase I study with ONCOS-102 for the treatment of solid tumors—an evaluation of clinical response and exploratory analyses of immune markers. *J Immunother Cancer* (2016) March 15; 4:17. doi: 10.1186/s40425-016-0121-5. eCollection 2016.

Romano E, Kusio-Kobialka M, Foukas P G, Baumgaertner P, Meyer C, Ballabeni P, Michielin O, Weide B, Romero P, Speiser D E. Ipilimumab-dependent cell-mediated cytotoxicity of regulatory T cells ex vivo by nonclassical monocytes in melanoma patients. *Proc Natl Acad Sci USA.* (2015) 112(19):6140-5. doi: 10.1073/pnas.1417320112.

Sagiv-Barfi I, Kohrt H E, Czerwinski D K, Ng P P, Chang B Y, Levy R. Therapeutic antitumor immunity by checkpoint blockade is enhanced by ibrutinib, an inhibitor of both BTK and ITK. *Proc Natl Acad Sci USA.* (2015) 112(9):E966-72. doi: 10.1073/pnas.1500712112.

Siurala M, Bramante S, Vassilev L, Hirvinen M, Parviainen S, Tahtinen S, Guse K, Cerullo V, Kanerva A, Kipar A, Vaha-Koskela M, Hemminki A. Oncolytic adenovirus and doxorubicin-based chemotherapy results in synergistic antitumor activity against soft-tissue sarcoma. *Int J Cancer* (2015) 136: 945-54.

Vassilev L, Ranki T, Joensuu T, Jager E, Karbach J, Wahle C, Partanen K, Kairemo K, Alanko T, Turkki R, Linder N, Lundin J, Ristimäki A, Kankainen M, Hemminki A, Backman C, Dienel K, von Euler M, Haavisto E, Hakonen T, Juhila J, Jäderberg M, Priha P, Vuolanto A, Pesonen S. Repeated intratumoral administration of ONCOS-102 leads to systemic antitumor CD8+ T-cell response and robust cellular and transcriptional immune activation at tumor site in a patient with ovarian cancer. *Oncoimmunology* (2015) April 1; 4(7):e1017702. eCollection 2015.

The invention claimed is:

1. A method of treating cancer in a human subject in need thereof, the method comprising administering ONCOS-102 adenovirus to the subject locally and administering a checkpoint inhibitor or checkpoint inhibitors to the subject systemically.

2. The method of claim 1, wherein the checkpoint inhibitor or checkpoint inhibitors are an anti-PD-1 antibody, an anti-PD-L1 antibody, or a combination thereof.

3. The method of claim 2, wherein the checkpoint inhibitor or checkpoint inhibitors is/are the anti-PD-1 antibody CT-011, the anti-PD-1 antibody pembrolizumab, the anti-PD-1 antibody nivolumab, the anti-PD-L1 antibody atezolizumab, the anti-PD-L1 antibody avelumab, the anti-PD-1 antibody lambrolizumab, the anti-PD-L1 antibody durvalumab, or a combination thereof.

4. The method of claim 2, wherein the checkpoint inhibitor or checkpoint inhibitors is/are the anti-PD-1 antibody pembrolizumab, the anti-PD-1 antibody nivolumab, the anti-PD-L1 antibody durvalumab, or a combination thereof.

5. The method of claim 4, wherein the checkpoint inhibitor is the anti-PD-L1 antibody durvalumab.

6. The method of claim 1, wherein the human cancer is selected from the group consisting of advanced melanoma, renal cancer, ovarian cancer, bladder cancer, prostate cancer, breast cancer, colorectal cancer, lung cancer, gastric cancer, classical Hodgkin lymphoma, mesothelioma, and liver cancer.

7. The method of claim 1, wherein the human cancer is advanced melanoma.

8. The method of claim 1, wherein the human cancer is an immune checkpoint inhibitor refractory cancer.

9. The method of claim 8, wherein the human cancer is a PD-1 inhibitor refractory cancer.

10. The method of claim 1, wherein the amount of the virus is from $5 \times 10^{10}$ to $5 \times 10^{11}$ VP per injection.

11. The method of claim 10, wherein the virus is administered in an amount of $3 \times 10^{11}$ VP per injection.

12. The method of claim 1, wherein the virus is administered before administering of the checkpoint inhibitor or checkpoint inhibitors.

13. The method of claim 12, wherein the virus is also administered during the administering period of said checkpoint inhibitor or checkpoint inhibitors.

14. The method of claim 12, wherein the virus is also administered after administering the checkpoint inhibitor or checkpoint inhibitors.

15. The method of claim 12, wherein the virus is also administered during the administering period of said checkpoint inhibitor or checkpoint inhibitors and the virus is also administered after administering the checkpoint inhibitor or checkpoint inhibitors.

16. The method of claim 1, wherein the virus is administered in multiple doses and the checkpoint inhibitor is administered in multiple doses to said subject.

17. The method of claim 1, wherein administering ONCOS-102 adenovirus to the subject locally comprises intratumoral or intracavity administration.

18. The method of claim 17, wherein the intracavity administration comprises intraperitoneal, intravesical, or intrapleural administration.

* * * * *